(12) United States Patent
Kracker et al.

(10) Patent No.: US 9,326,711 B2
(45) Date of Patent: May 3, 2016

(54) OPTICAL PERFUSION SENSOR DETECTOR

(75) Inventors: Stefan G. Kracker, Sonthofen (DE); Sourav Kumar Bhunia, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 2126 days.

(21) Appl. No.: 12/164,491

(22) Filed: Jun. 30, 2008

(65) Prior Publication Data

US 2009/0326346 A1    Dec. 31, 2009

(51) Int. Cl.
| | |
|---|---|
| *A61B 5/145* | (2006.01) |
| *A61B 5/1459* | (2006.01) |
| *A61B 5/00* | (2006.01) |
| A61B 5/1455 | (2006.01) |
| A61N 1/08 | (2006.01) |
| A61N 1/37 | (2006.01) |

(52) U.S. Cl.
CPC ........... *A61B 5/14542* (2013.01); *A61B 5/1459* (2013.01); *A61B 5/6846* (2013.01); *A61B 5/14552* (2013.01); *A61N 1/08* (2013.01); *A61N 1/37* (2013.01)

(58) Field of Classification Search
CPC ............. A61B 5/1455; A61B 5/14551; A61B 5/14552; A61B 5/14553; A61B 5/1459; A61B 5/14542; A61B 5/0031; A61B 2562/04; A61B 2562/043; A61B 2562/046
USPC ................. 600/322–327, 331–334, 336–337, 600/339–341, 363
See application file for complete search history.

(56) References Cited

U.S. PATENT DOCUMENTS

| | | |
|---|---|---|
| 4,374,382 A | 2/1983 | Markowitz |
| 4,903,701 A | 2/1990 | Moore et al. |
| 4,911,167 A | 3/1990 | Corenman et al. |
| 4,934,372 A | 6/1990 | Corenman et al. |
| 5,040,533 A | 8/1991 | Fearnot |
| 5,431,170 A | 7/1995 | Mathews |
| 5,556,421 A | 9/1996 | Prutchi et al. |
| 5,795,300 A | 8/1998 | Bryars |
| 6,122,536 A * | 9/2000 | Sun et al. ...................... 600/341 |
| 6,125,290 A | 9/2000 | Miesel |

(Continued)

OTHER PUBLICATIONS

U.S. Appl. No. 12/181,025, entitled "Implantable Optical Hemodynamic Sensor Including Light Transmission Member", filed Jul. 28, 2008.

(Continued)

*Primary Examiner* — Adam J Eiseman
(74) *Attorney, Agent, or Firm* — Evans M. Mburu; Stephen W. Bauer

(57) ABSTRACT

A reflectance optical perfusion sensor may include at least one light source and a plurality of detector elements arranged in a planar or nonplanar configuration, such as a three-dimensional array. The detector elements may sense light emitted by the at least one light source and reflected by a blood mass of a patient, such as blood within a blood vessel. In some examples, the detector elements may be arranged such that photodetection surfaces of at least two of the detector elements are nonparallel. In addition to or instead of the nonplanar arrangement of detector elements, an optical perfusion sensor may include a detector array including a plurality of detector elements at least partially surrounding a light source. Varying the location and orientations of detector elements may help increase a quantity of light emitted by the at least one light source and reflected toward the optical perfusion sensor by blood.

26 Claims, 10 Drawing Sheets

(56) References Cited

U.S. PATENT DOCUMENTS

| | | | |
|---|---|---|---|
| 6,160,478 | A | 12/2000 | Jacobsen et al. |
| 6,198,952 | B1 | 3/2001 | Miesel |
| 6,331,162 | B1 | 12/2001 | Mitchell |
| 6,491,639 | B1 | 12/2002 | Turcott |
| 6,783,498 | B2 | 8/2004 | Sackner et al. |
| 7,072,702 | B2 | 7/2006 | Edgar, Jr. et al. |
| 7,120,481 | B2 | 10/2006 | Keller et al. |
| 7,142,906 | B2 | 11/2006 | Yamashita et al. |
| 7,286,884 | B2 | 10/2007 | Marshall et al. |
| 7,302,294 | B2 | 11/2007 | Kamath et al. |
| 7,376,454 | B2 | 5/2008 | Casciani et al. |
| 2006/0253160 | A1 | 11/2006 | Benditt et al. |
| 2007/0016089 | A1 | 1/2007 | Fischell et al. |
| 2007/0150017 | A1 | 6/2007 | Salo |
| 2007/0156085 | A1 | 7/2007 | Schulhauser |
| 2007/0179366 | A1 | 8/2007 | Pwezner et al. |
| 2007/0239053 | A1 | 10/2007 | Bhunia |
| 2007/0239215 | A1 | 10/2007 | Bhunia |
| 2008/0091242 | A1 | 4/2008 | Kamath et al. |
| 2008/0208020 | A1* | 8/2008 | Cinbis et al. .................. 600/323 |
| 2009/0270953 | A1* | 10/2009 | Ecker et al. ..................... 607/88 |

OTHER PUBLICATIONS

U.S. Appl. No. 12/164,776, entitled "Tissue Perfusion Sensor Control", filed Jun. 30, 2008.

U.S. Appl. No. 12/164,835, entitled "Cardiac Signal Sensor Control", filed Jun. 30, 2008.

U.S. Appl. No. 12/182,847, entitled "Physiological Parameter Monitoring With Minimization of Motion Artifacts", filed Jul. 30, 2008.

\* cited by examiner

OPTICAL PERFUSION SENSOR DETECTOR

TECHNICAL FIELD

The disclosure relates to medical devices, and, more particularly, to medical devices that monitor one or more physiological parameters of a patient.

BACKGROUND

Some medical devices may monitor one or more hemodynamic characteristics of a patient, such as the blood oxygen saturation level in arterial blood, the volume of blood supplying a particular tissue site, and the like. Example medical devices that monitor hemodynamic characteristics of a patient include pulse oximeters. One type of pulse oximeter, which may also be referred to as an optical perfusion sensor, includes at least one light source that emits light through a portion of blood-perfused tissue of a patient, and a detector that senses the emitted light that passed through the blood-perfused tissue. An intensity of the light sensed by the detector may be indicative of hemodynamic function of the patient, such as oxygen saturation of blood of the patient.

In some types of optical perfusion sensors, the one or more light sources may be positioned on the same side of the blood perfused tissue as the detector, such that the detector detects light emitted by the light sources and reflected by blood. This type of optical perfusion sensor may be referred to as a reflectance optical perfusion sensor. In other types of optical perfusion sensors, referred to as transmissive perfusion sensors, the one or more light sources may oppose the detector, such that the detector senses light that is transmitted through the blood perfused tissue.

SUMMARY

In some aspects, the disclosure is directed toward an optical perfusion sensor that includes a detector array including a plurality of detector elements. The detector elements may each generate a signal indicative of an intensity of light incident on the detector element. For example, at least some of the detector elements of the detector array may include a photodiode that converts light into either an electrical current or voltage. In some examples, the optical perfusion sensor is a reflectance optical perfusion sensor that includes one or more light sources that emit light and a detector array comprising a plurality of detector elements to detect the light emitted by the one or more light sources and reflected by a blood mass (e.g., blood cells in a patient's blood vessel). Thus, in some examples, the detector array and one or more light sources may be positioned on a common side of a housing of the optical perfusion sensor.

In some examples described herein, a plurality of detector elements are arranged in a nonplanar configuration, such that the detector elements are positioned at varying distances, and, in some examples, varying angles relative to at least one light source of the optical perfusion sensor. For example, the detector elements may be arranged in a three-dimensional array. A nonplanar configuration of detector elements may help diversify the angles of incidence, as well as the locations of the detector elements in order to increase a probability of sensing light emitted by the one or more light sources and reflected by a blood mass. In some cases, an optical perfusion sensor including a plurality of detector elements, which may or may not be arranged in a nonplanar array, may also help increase the quantity (e.g., percentage) of light reflected by blood that is detected by the optical perfusion sensor, which may improve the signal to noise ratio of the optical perfusion sensor.

In other aspects, the disclosure is directed toward an optical perfusion sensor that includes a detector that at least partially surrounds a light source, where the detector is configured to sense light that is reflected by a blood mass. The detector may include a detector array including a plurality of detector elements or single detector. For example, an array of detector elements may at least partially surround the one or more light sources of the reflectance optical perfusion sensor on a common side of a housing of the optical perfusion sensor. As another example, a detector may be an annulus or a partial annulus that is positioned around the light source. In some examples, the array of detector elements that at least partially surround the one or more light sources may define a substantially two-dimensional array, while in other examples, the detector elements may define a three-dimensional array.

In one aspect, the disclosure is directed to an implantable medical device comprising a light source, and a plurality of detector elements arranged in a nonplanar configuration. Each detector element of the plurality of detector elements is configured to sense light emitted by the light source and reflected onto the respective detector element.

In another aspect, the disclosure is directed to an implantable medical device comprising a light source, and a detector that at least partially surrounds the light source. The detector is configured to generate a signal indicative of an intensity of light emitted by the light source and reflected onto the detector. In some examples, the detector comprises a plurality of detector elements positioned on at least two sides of the light source.

In another aspect, the disclosure is directed to a method comprising transmitting light from a light source positioned on a side of a housing of an implantable medical device and receiving the light at a detector positioned on the side of the housing, wherein the detector comprises a plurality of detector elements arranged in a nonplanar configuration.

In another embodiment, the invention is directed to a computer-readable medium containing instructions. The instructions cause a programmable processor to perform any part of the techniques described herein.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
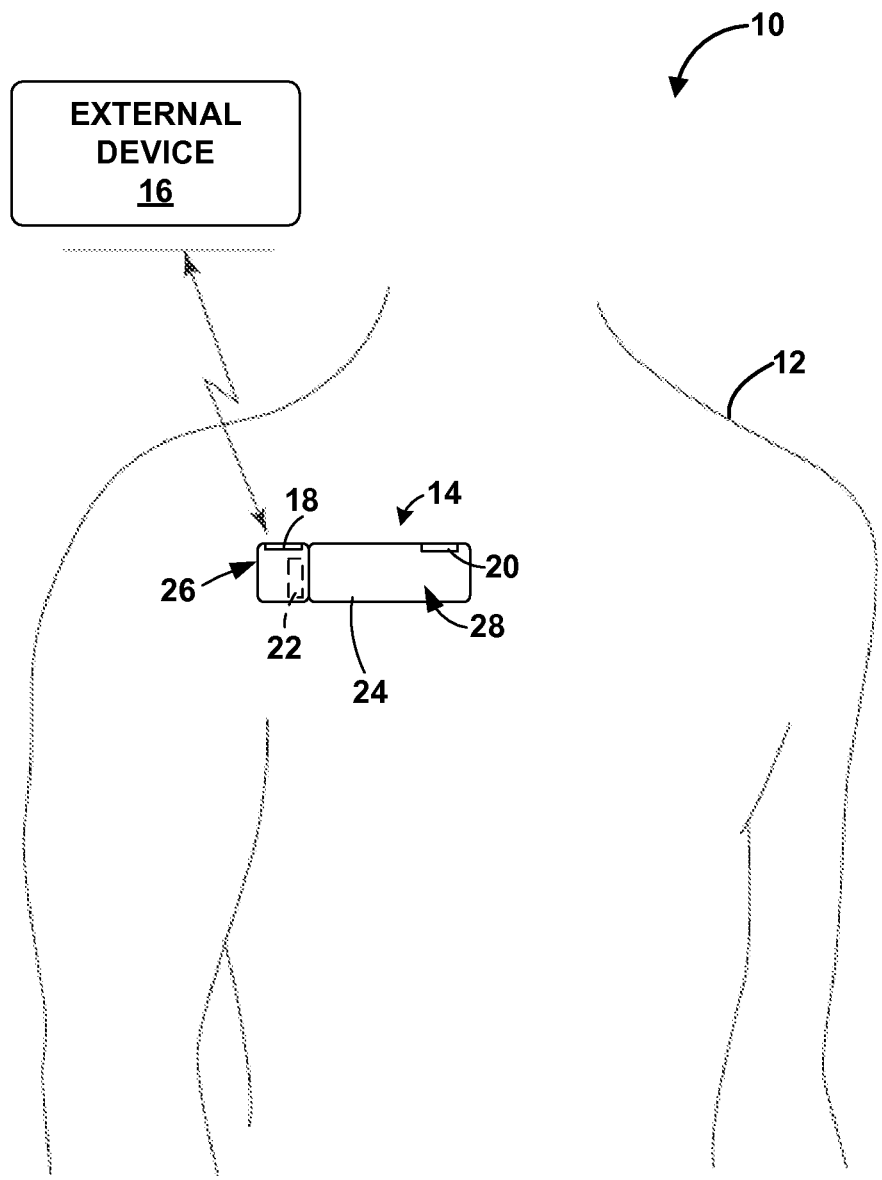
FIG. 1 is a conceptual diagram illustrating an example monitoring system that includes an implantable medical device (IMD) including an optical perfusion sensor.

FIG. 1 is a conceptual diagram illustrating an example monitoring system 10 that may be used to monitor one or more physiological parameters of patient 12, such as cardiac signals of a heart of patient 12 and an oxygen saturation level of blood of patient 12. Patient 12 ordinarily, but not necessarily, will be a human. Monitoring system 10 includes implantable medical device (IMD) 14 and external device 16. IMD 14 may be, for example, an implantable cardiac monitor that does not provide therapy (e.g., stimulation therapy) to patient 12. IMD 14 may also be referred to as an implantable monitor. In other examples, e.g., as described with respect to FIG. 2, IMD 14 may be configured to deliver stimulation to the heart of patient 12 or to deliver another type of therapy to patient 12 (e.g., delivery of a therapeutic agent). Neither IMD 14 nor external device 16 or any of the figures shown herein are drawn to any particular scale.

In the example shown in FIG. 1, IMD 14 is implanted within a subcutaneous tissue layer of patient 12. Due to its relatively small size, a clinician may implant monitor 14 through a relatively small incision in the patient's skin, or percutaneously, e.g., via an introducer. In other examples, IMD 14 may be implanted within other tissue sites, such as a submuscular location. IMD 14 may be a temporary diagnostic tool employed to monitor one or more physiological parameters of patient 12 for a relatively short period of time (e.g., days or weeks), or may be used on a more permanent basis, such as to control therapy delivery to patient 12. In some examples of the latter use of IMD 14, a separate therapy delivery device, such as a fluid delivery device, pacemaker, cardioverter or defibrillator, may be implanted within patient 12. The therapy delivery device may communicate with IMD 14 via a wired connection or via wireless communication techniques. In other examples, as previously described, IMD 14 may be incorporated in a common housing with a therapy delivery device.

IMD 14 includes electrodes 18, 20 that sense electrical activity of patient's heart. For example, IMD 14 may generate an electrogram (EGM) or electrocardiogram (ECG) based on signals from electrodes 18, 20. While other types of electrical signals of the heart of patient 12 are contemplated, EGM signals are primarily referred to throughout the remainder of the disclosure. Electrodes 18, 20 may be positioned any suitable distance from each other. In the example shown in FIG. 1, electrodes 18, 20 are coupled to an outer housing 24 of IMD 14. In other examples, electrodes 18, 20 may be coupled to leads that extend from outer housing 24 of IMD 14.

IMD 14 further includes optical perfusion sensor 22 that generates a signal indicative of the blood oxygen saturation level of blood in a tissue site proximate to optical perfusion sensor 22. The blood oxygen saturation level may be indicative of various hemodynamic characteristics, such as blood pressure of patient 12 or a relative blood flow through the tissue site. Examples of optical perfusion sensors are described below with reference to FIGS. 5A-10B. Although optical perfusion sensor 22 and electrodes 18, 20 are shown to be on different sides of housing 24 of IMD 14, in other examples, optical perfusion sensor 22 may be on the same side of housing 24 with at least one of the electrodes 18, 20.

In the example shown in FIG. 1, optical perfusion sensor 22 is positioned on header 26 of IMD 14. In other examples, optical perfusion sensor 22 may be positioned on case 28 of IMD 14. Case 28 may be hermetically sealed and may enclose various sensing and control circuitry for sensing one or more physiological parameters of patient 12, and, in some cases, a therapy delivery module for delivering therapy to patient 12 (e.g., electrical stimulation or a therapeutic agent). Header 26 may provide a hermetically sealed passage for connecting electrode 18 and optical perfusion sensor 22 to components within case 28.

In other examples of IMD 14, IMD 14 may not include a separate header 26 and case 28. IMD 14 may be implanted within patient 12 such that optical perfusion sensor 22 is adjacent to blood-perfused tissue. For example, optical perfusion sensor 22 may be positioned proximate to tissue that is near vasculature of patient 12 (e.g., one or more blood vessels), but not within a vein, artery, or heart of patient 12. In other examples, optical perfusion sensor 22 may be positioned within a vein or other vasculature of patient 12.

As described in further detail below with reference to FIG. 3, in some examples, optical perfusion sensor 22 includes at least one light source that emits light at a particular wavelength, which scatters through blood-perfused tissue, and a detector array comprising a plurality of detector elements that are each configured to sense light that emitted from the light source and reflected by a blood mass (e.g., blood cells in a blood vessel or artery of patient 12). In some examples, optical perfusion sensor 22 includes at least two light sources that emit light at different wavelengths, where at least two detector elements of the detector array may be sensitive to different wavelengths of light. In other examples, as described with reference to FIGS. 10A and 10B, optical perfusion sensor 22 may include a single detector that at least partially surrounds a light source.

Oxygenated and deoxygenated hemoglobin within the blood may absorb different wavelengths of light unequally. Accordingly, the intensity of light that is emitted by the light source of sensor 22 and reflected by blood may indicate relative blood oxygen saturation levels. At least some of the light reflected by the blood may be detected by the detector array of optical perfusion sensor 22. As described in further detail below with reference to FIGS. 5A and 5B, the detector array of optical perfusion sensor 22 may include a plurality of detector elements that are positioned on to at least partially surround a light source of optical perfusion sensor 22, such that the detector array may detect reflected light at two different locations. In addition to or instead of the detector array that at least partially surrounds a light source, the detector array may include a nonplanar array of detector elements. The detector array including a nonplanar array and/or detector elements arranged to at least partially surround a light source may help increase the probability that light reflected by blood of the patient is detected by the detector array.

The arrangement of the detector elements of a detector array described herein increases the probability of capturing light reflected by the patient's blood. In addition, a detector array including a plurality of detector elements and/or a nonplanar detector array may also help increase the overall quantity and quality of reflected light that is sensed by optical perfusion sensor 22. This may help increase the signal to noise ratio of optical perfusion sensor 22

In some examples, IMD 14 may be implanted within patient 12 such that optical perfusion sensor 22, or at least the light source and detector array, face away from the epidermis of patient 12 in order to help minimize interference from background light, e.g., from outside of the patient's body. Background light may include light from a source other than the one or more light sources of optical perfusion sensor 22. Detection of the background light by the detector elements of the detector array of optical perfusion sensor 22 may result in an inaccurate and imprecise reading of the level of blood oxygen saturation of the adjacent tissue.

The optical properties of blood-perfused tissue may change depending upon the relative amounts of oxygenated and deoxygenated hemoglobin due, at least in part, to their different optical absorption spectra. That is, the oxygen saturation level of the patient's blood may affect the amount of light that is absorbed by a blood mass and the amount of light that is reflected by the blood mass. Accordingly, an electrical signal generated by optical perfusion sensor 22 that indicates the intensity of one or more wavelengths of light detected by the detector of sensor 22 may change based on the relative amounts of oxygenated and deoxygenated hemoglobin in the tissue.

The signal generated by optical perfusion sensor 22 may indicate the relative change in hemoglobin of the blood-perfused tissue that is saturated with oxygen as well as the change in hemoglobin concentration in the tissue. An O2 variation index may be calculated based on the intensity of light detected by plurality of detector elements of optical perfusion sensor 22. An O2 variation index may also be referred to as an O2 index or an optical oxygenation index. The O2 variation index may indicate a change in blood oxygenation of the tissue adjacent to optical perfusion sensor 22. Example techniques for determining an O2 variation index are described in U.S. Patent Application Publication No. 2007/0239053 to Bhunia, entitled, "METHOD AND APPARATUS FOR VERIFYING A DETERMINED CARDIAC EVENT IN A MEDICAL DEVICE BASED ON DETECTED VARIATION IN HEMODYNAMIC STATUS," which was filed on Apr. 28, 2006 and is incorporated herein by reference in its entirety.

Changes in blood oxygenation of the tissue adjacent to optical perfusion sensor 22 may indicate various hemodynamic characteristics of patient 12. For example, hemodynamic characteristics of a cardiac rhythm of patient 12 may be derived from a signal generated by optical perfusion sensor 22. In some cases, the signal generated by optical perfusion sensor 22 may indicate the blood oxygen saturation level of the adjacent tissue or the body of patient 12 as a whole. In some cases, changes in blood pressure may be derived from the changes in the blood oxygen saturation level. As used herein, "tissue perfusion" may also refer to the concentration of oxygen in blood within the tissue. Accordingly, tissue perfusion and blood oxygenation levels are interchangeably referred to in the present disclosure.

The presence of cardiac arrhythmias may be derived from a signal generated by optical perfusion sensor 22. As described in U.S. Patent Application Publication No. 2007/0239053 to Bhunia et al., a signal based on the O2 variation index may indicate any change in hemodynamic status. A monotonically decreasing trend in the O2 Variation Index at the onset of a cardiac arrhythmia may confirm the event to be hemodynamically unstable, as in case of ventricular fibrillation.

In addition, as described in U.S. Patent Application Publication No. 2007/0239215 to Bhunia et al., entitled, "METHOD AND APPARATUS FOR USING AN OPTICAL HEMODYNAMIC SENSOR TO IDENTIFY AN UNSTABLE ARRHYTHMIA," which was filed on Mar. 31, 2006 and is incorporated herein by reference in its entirety, electrical signals generated by a detector of an optical perfusion sensor may experience a significant change in value following a hemodynamically unstable ventricular fibrillation. In one example provided by U.S. Patent Application Publication No. 2007/0239215 to Bhunia et al., an optical perfusion sensor includes a red light emitting diode (LED) and an infrared (IR) LED as light sources, and a detector. An increase in a red optical signal sensed by a detector, which may indicate the amount of red light from the red LED that traversed through the blood-perfused tissue, and a decrease in an IR signal sensed by the detector, which may indicate the amount of IR light from the IR LED that traversed through the blood-perfused tissue, may indicate the occurrence of a cardiac arrhythmia.

In the present disclosure, the plurality of detector elements of the detector array of optical perfusion sensor 22 are arranged within sensor 22 to help increase the amount of light emitted by the one or more light sources of sensor 22 and reflected by a blood mass (or generally "blood) that is sensed by the detector array. As described in further detail below with reference to FIGS. 5A-9B, the detector array may include a plurality of detector elements (e.g., photodiodes). In some examples, the plurality of detector elements may be positioned to at least partially surround the one or more light sources of optical perfusion sensor, e.g., detector elements may be on at least two sides of the one or more light sources of optical perfusion sensor 22. The detector array and one or more light sources may be positioned on the same side of housing 24 of IMD 14. In other examples, as described with reference to FIGS. 10A and 10B, optical perfusion sensor 22 may include a single detector that at least partially or fully surrounds a light source.

In addition to or instead of a detector array at least partially surrounding one or more light sources, in some examples, the detector array of optical perfusion sensor 22 may include detector elements that are arranged in a nonplanar configuration, such as a two-dimensional (2D) or a three-dimensional (3D) array. In the nonplanar arrangement, the detector elements may be positioned at substantially the same or various distances and at substantially the same or various angles relative to the one or more light sources of optical perfusion sensor 22. The light that is emitted by the one or more light sources may be reflected by blood, and the reflected light may be sensed by the plurality of detector elements of the detector array. In a 2D array, at least some of the detector elements of the detector array may have different spatial positions in two dimensions. For example, at least some of the detector elements may lie in a common plane, but have different locations in two different dimensions. In a 3D array, at least some of the detector elements of the detector array may have different spatial positions in at least three different dimensions.

Positioning detector elements (or a single detector element) to at least partially surround a light source of the reflectance optical perfusion sensor and/or in a nonplanar configuration may help to increase the probability that a detector element of the detector array may sense light that has been reflected by blood. The light emitted by the one or more light sources of optical perfusion sensor 22 may be scattered by the patient's tissue, and the emitted light that is reflected by blood may not be focused in any particular direction. Thus, a detector positioned on one side of a light source or a single detector having a relatively small photodetection surface area may only receive a small percentage of the light that has been reflected by blood. Optical perfusion sensor 22 includes a single detector that extends at least partially around the one or more light sources or a plurality of detector elements that are positioned on different sides of the one or more light sources and/or in a planar or nonplanar configuration, thereby increasing the diversity of detector elements locations and increasing the probability that the detector array will sense light reflected by blood that is detected by the detector array of optical perfusion sensor 22 and, in some cases, also increase the percentage of light reflected by blood that is detected by the detector array of optical perfusion sensor 22.

As described in further detail below with reference to FIG. 3, IMD 14 may include a memory that stores EGM signals and tissue perfusion information (e.g., electrical signals generated by optical perfusion sensor 22 or data derived from the electrical signal). In addition or alternatively, IMD 14 may transmit the EGM signals and tissue perfusion information to an external device, such as external device 16. In some examples, IMD 14 may store the tissue perfusion information that corresponds in time to the sensed EGM signals (or other cardiac signals), thereby allowing a clinician to determine the patient's cardiac activity at the time a particular blood oxygen saturation level was observed, or to determine the patient's blood oxygen saturation level at the time a particular cardiac activity was observed. Accordingly, the tissue perfusion information and cardiac signal information generated by IMD 14 may be later retrieved and analyzed by a clinician. In some examples, a clinician may retrieve stored EGM and tissue perfusion information from IMD 14 after explanting monitor 14 from patient 12. In other examples, the clinician (or other user) may interrogate monitor 14 with external device 16 while monitor 14 remains implanted within patient 12 in order to retrieve stored information from IMD 14.

IMD 14 may be useful for monitoring physiological parameters, such as the EGM and blood pressure, of patient 12. The monitored physiological parameter values may provide useful information for diagnosing a patient condition or formulating a treatment plan for patient 12. For example, if patient 12 experiences syncope, e.g., periodic fainting, IMD 14 may be used to determine the physiological parameters that are associated with the syncope events. A clinician may review the associated physiological parameters to determine a potential cause of the syncopic events. For example, a clinician may determine whether any patient events occurred based on the recorded signals from optical perfusion sensor 22, and, in some cases, recorded cardiac signals.

In some cases, syncope may be triggered by a cardiac arrhythmia, such as a bradycardia event or episode, which includes more than one event. A bradycardia event may be determined, e.g., based on a duration of a cardiac cycle. A cardiac cycle duration may be, for example, measured between successive R-waves or P-waves of the EGM signal. This duration may also be referred to as an R-R or P-P interval.

In other cases, syncope may be triggered by other patient conditions, such as neurocardiogenic syndrome, which may be a dysregulation of the peripheral and/or central autonomous nervous system. Neurocardiogenic syncope may also be referred to as neurogenic syncope, vasovagal syncope or neutrally mediated syncope. In patients with neurocardiogenic syndrome, blood vessels may expand, which may result in a decrease in blood volume that reaches the patient's brain. Such a decrease in blood volume may cause a syncope event. In some cases, neurocardiogenic syncope may occur due to emotionally stressful events or physical exercise, although other triggering circumstances are also possible.

The oxygen concentration of blood in tissue of patient 12 may change in response to a change in a cardiac arrhythmia event or episode. However, in some cases, there may be a delay between the start of the cardiac arrhythmia event and the change in tissue perfusion (e.g., change in blood oxygen saturation level) (e.g., as reflected by a change in the blood oxygen saturation level). For example, a cardiac signal (e.g., an ECG or EGM signal) may reflect a cardiac arrhythmia event or episode before the tissue perfusion change is detected. This delay between the detection of a cardiac event and an observed change of tissue perfusion may be useful for diagnosing the cause of a patient's syncope event. In some cases, a clinician may review tissue perfusion information and cardiac signal information stored in IMD 14 to determine whether a change in tissue perfusion of tissue occurred after a cardiac arrhythmia event or before the cardiac arrhythmia event. If the change in tissue perfusion occurred after the cardiac arrhythmia event was detected, the clinician may determine that the physiological parameter values of patient 12 suggest that a syncope event that occurred substantially at the same time as the cardiac arrhythmia may be at least partially attributable to the cardiac arrhythmia. On the other hand, if the change in tissue perfusion occurred before the cardiac arrhythmia event was detected, the clinician may determine that the physiological parameter values of patient 12 suggest that a syncope event was attributable to a source other than to the cardiac arrhythmia.

External device 16 may be a handheld computing device or a computer workstation. External device 16 may include a user interface that receives input from a user, such as a clinician. The user interface may include, for example, a keypad and a display, which may for example, be a cathode ray tube (CRT) display, a liquid crystal display (LCD) or LED display. The keypad may take the form of an alphanumeric keypad or a reduced set of keys associated with particular functions. External device 16 can additionally or alternatively include a peripheral pointing device, such as a mouse, via which a user may interact with the user interface. In some embodiments, a display of external device 16 may include a touch screen display, and a user may interact with external device 16 via the display.

A user, such as a physician, technician, or other clinician, may interact with external device 16 to communicate with IMD 14. For example, the user may interact with external device 16 to retrieve physiological or diagnostic information from IMD 14. A user may also interact with external device 16 to program IMD 14, e.g., select values for operational parameters of monitor 14.

For example, the user may use external device 16 to retrieve information from IMD 14 regarding the rhythm of the heart of patient 12 (e.g., determined based on an EGM signal), trends of the heart rhythm over time, or arrhythmia episodes. As another example, the user may use external device 16 to retrieve information from IMD 14 regarding other sensed physiological parameters of patient 12, such as tissue perfusion data, activity, posture, respiration, or thoracic impedance. As another example, the user may use external device 16 to retrieve information from IMD 14 regarding the performance or integrity of IMD 14.

IMD 14 and external device 16 may communicate via wireless communication using any techniques known in the art. Examples of communication techniques may include, for example, low frequency or radiofrequency (RF) telemetry, but other techniques are also contemplated. In some examples, external device 16 may include a programming head that may be placed proximate to the patient's body near the implant site of IMD 14 in order to improve the quality or security of communication between IMD 14 and external device 16.

In other examples, IMD 14 may not include electrodes 18, 20 for monitoring cardiac signals of the heart of patient 12. For example, IMD 14 may only include optical perfusion sensor 22 that monitors hemodynamic function of patient 12, such as the blood oxygen saturation level of arterial blood or blood pressure of patient 12. The detector arrays described herein may be useful with any suitable type of optical sensor that senses light. Accordingly, while IMD 14 including EGM and pulse oximeter capabilities is primarily referred to herein, in other examples, the nonplanar detector array including a plurality of detector elements may be incorporated into other types of optical sensors.

Figure 2:
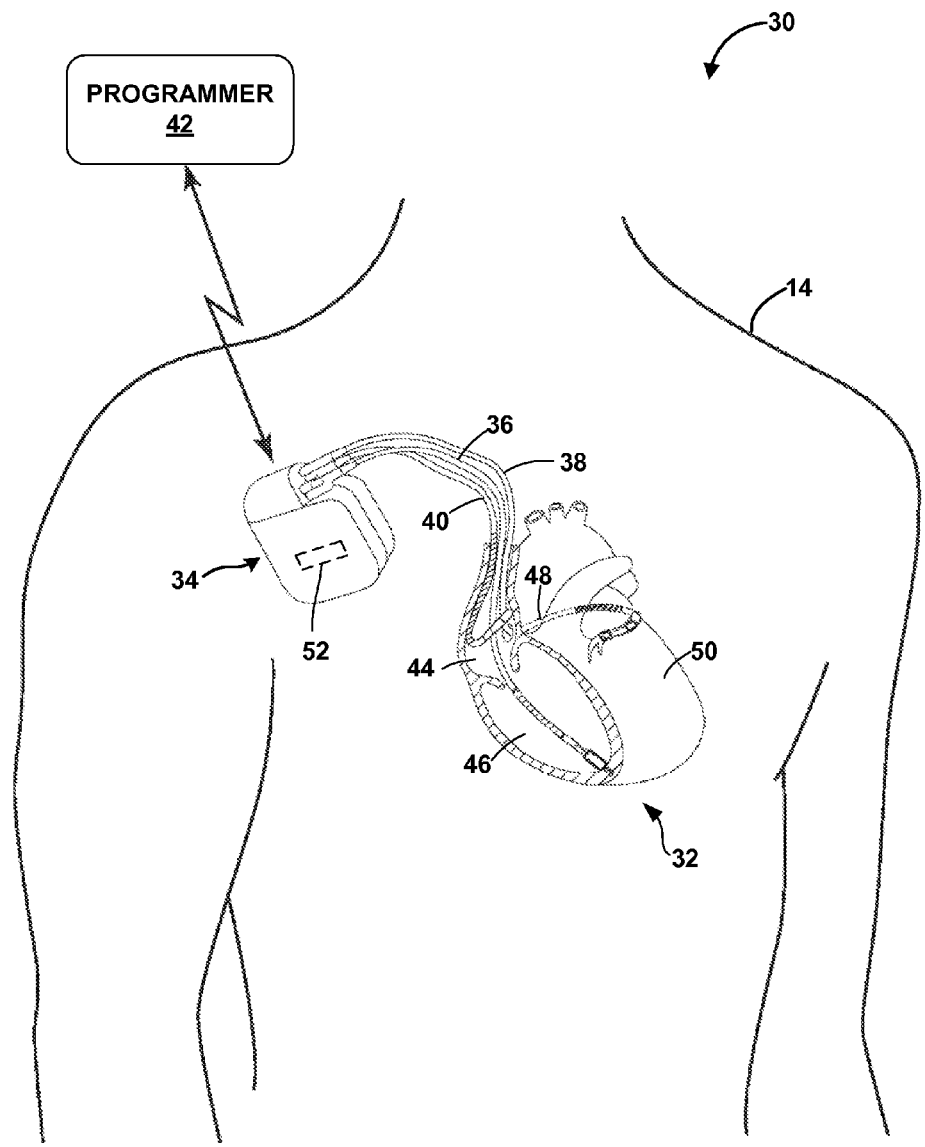
FIG. 2 is a conceptual diagram illustrating an example therapy system that includes an IMD that delivers therapy to a patient, where the medical device includes a tissue perfusion sensor.

FIG. 2 is a conceptual diagram illustrating an example therapy system 30 that may be used to provide therapy to heart 32 of patient 12. Therapy system 30 includes IMD 34 that provides therapy to patient 12. IMD 34 is coupled to leads 36, 38, and 40, and programmer 42. IMD 34 may be, for example, an implantable pacemaker, cardioverter, and/or defibrillator that provides electrical signals to heart 32 via electrodes coupled to one or more of leads 36, 38, and 40.

Leads 36, 38, 40 extend into the heart 32 of patient 12 to sense electrical activity of heart 32 and/or deliver electrical stimulation to heart 32. In the example shown in FIG. 2, right ventricular (RV) lead 36 extends through one or more veins (not shown), the superior vena cava (not shown), and right atrium 44, and into right ventricle 46. Left ventricular (LV) coronary sinus lead 38 extends through one or more veins, the vena cava, right atrium 44, and into the coronary sinus 48 to a region adjacent to the free wall of left ventricle 50 of heart 32. Right atrial (RA) lead 40 extends through one or more veins and the vena cava, and into the right atrium 44 of heart 32.

IMD 34 may sense electrical signals attendant to the depolarization and repolarization of heart 32 via electrodes (not shown in FIG. 2) coupled to at least one of the leads 36, 38, 40. In some examples, IMD 34 provides pacing pulses to heart 32 based on the electrical signals sensed within heart 32. The configurations of electrodes used by IMD 34 for sensing and pacing may be unipolar or bipolar. IMD 34 may also provide defibrillation therapy and/or cardioversion therapy via electrodes located on at least one of the leads 36, 38, 40. IMD 34 may detect arrhythmia of heart 32, such as fibrillation of ventricles 46, 50, and deliver defibrillation therapy to heart 32 in the form of electrical pulses. In some examples, IMD 34 may be programmed to deliver a progression of therapies, e.g., pulses with increasing energy levels, until a fibrillation of heart 32 is stopped. IMD 34 detects fibrillation employing one or more fibrillation detection techniques known in the art.

IMD 34 includes optical perfusion sensor 52, which is similar to optical perfusion sensor 22 described above with respect to FIG. 1. IMD 34 may include features similar to those described with respect to IMD 14. Accordingly, the examples of planar and nonplanar detector arrays described herein with reference to optical perfusion sensor 22 of IMD 14 (FIG. 1) are also applicable to the optical perfusion sensor 52 of IMD 34.

In some examples, programmer 42 may be similar to external device 16 of monitoring system 10 (FIG. 1). In addition, a user may use programmer 42 to program a therapy progression, select electrodes used to deliver defibrillation pulses, select waveforms for the defibrillation pulse, or select or configure a fibrillation detection algorithm for IMD 34. The user may also use programmer 42 to program aspects of other therapies provided by IMD 34, such as cardioversion or pacing therapies. In some examples, the user may activate certain features of IMD 34 by entering a single command via programmer 42, such as depression of a single key or combination of keys of a keypad or a single point-and-select action with a pointing device.

IMD 34 and programmer 42 may communicate via wireless communication using any techniques known in the art. Examples of communication techniques may include, for example, low frequency or radiofrequency (RF) telemetry, but other techniques are also contemplated. In some examples, programmer 42 may include a programming head that may be placed proximate to the patient's body near the IMD 34 implant site in order to improve the quality or security of communication between IMD 34 and programmer 42.

Figure 3:
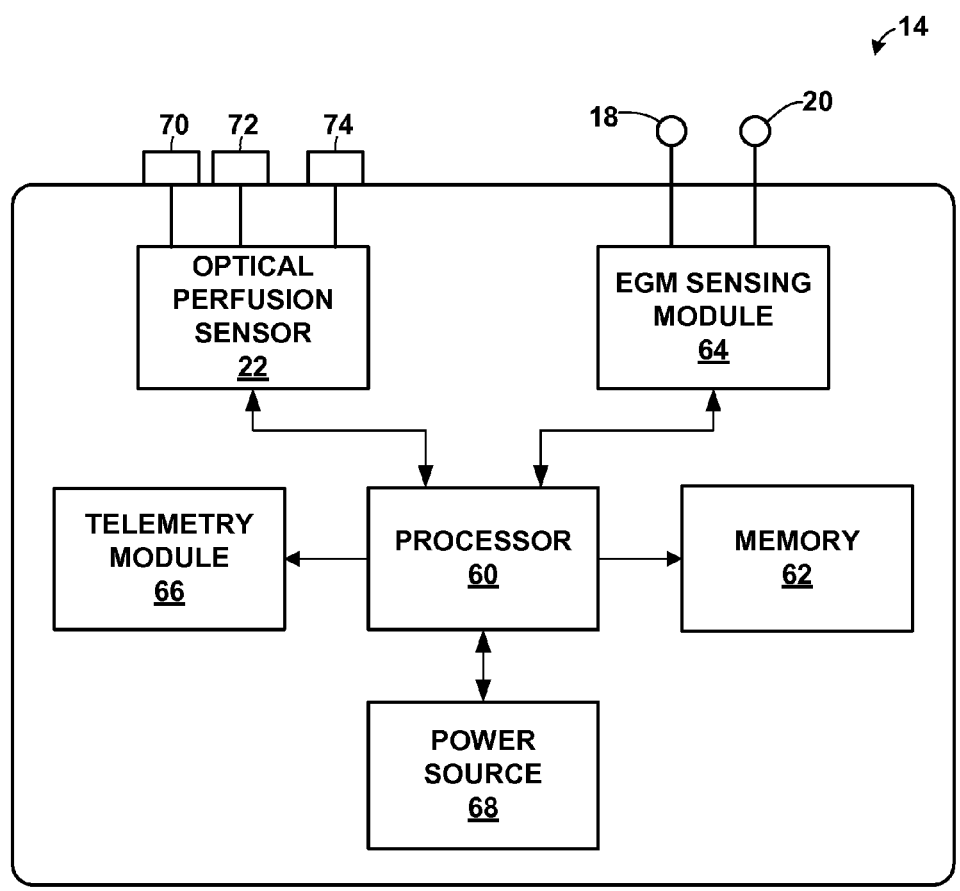
FIG. 3 is a functional block diagram of an example IMD that includes an optical tissue perfusion sensor.

FIG. 3 is a block diagram of an example IMD 14. In the example shown in FIG. 3, IMD 14 includes optical perfusion sensor 22, processor 60, memory 62, EGM sensing module 64, telemetry module 66, and power source 68. Memory 62 includes computer-readable instructions that, when executed by processor 60, cause IMD 14 and processor 60 to perform various functions attributed to IMD 14 and processor 60 herein. Memory 62 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 60 may include one or more microprocessors, controllers, digital signal processors (DSPs), application specific integrated circuits (ASICs), field-programmable gate arrays (FPGAs), or equivalent discrete or integrated logic circuitry, or combinations thereof. In some examples, processor 60 may include multiple components, such as any combination of one or more microprocessors, one or more controllers, one or more DSPs, one or more ASICs, or one or more FPGAs, as well as other discrete or integrated logic circuitry. The functions attributed to processor 60 herein may be embodied as software, firmware, hardware or any combination thereof. Processor 60 may control EGM sensing module 64 to sense EGM signals of heart 32 of patient 12 (FIG. 2) and may store EGM signals from EGM sensing module 64 in memory 62.

In some examples, optical perfusion sensor 22 may include two or more light sources for producing at least two different wavelengths of light, while in other examples, sensor 22 may include a single light source that produces light at a single wavelength. In the example shown in FIG. 3, optical perfusion sensor 22 includes red LED 70, IR LED 72, and detector array 74, which includes a plurality of detector elements (not shown) arranged in a nonplanar configuration. In other examples, optical perfusion sensor 22 may include a single detector that at least partially surrounds red LED 70 and IR LED 72, as discussed with respect to FIGS. 10A-10B. Thus, while detector array 74 is primarily referred to throughout the description of FIG. 3, in other examples, sensor 22 may include a single detector that partially or fully surrounds red LED 70 and IR LED 72.

Red LED 70 may emit light in the red portion of the visible light spectrum, and IR LED 72 may emit IR light in the IR portion of the light spectrum. As described in further detail below with reference to FIGS. 5A-9B, detector array 74 includes a plurality of detector elements that are each configured to detect light emitted from red LED 70 and IR LED 72 and reflected by blood of the patient. Blood that reflects the emitted light may include, for example, a blood mass in a blood vessel, artery or other vasculature of patient 12. In some examples, at least one of the detector elements may be sensitive to wavelengths of light in the red portion of the visible spectrum, and at least one of the detector elements may be sensitive to wavelengths of light in the IR portion of the light spectrum. In other examples, the detector elements of detector array 74 may be configured to sense light in both the red portion and IR portion of the light spectrum.

The detector elements may each include, for example, a photodetector, such as a photodiode. In some examples, the detector elements may convert light incident on a detection surface of the detector element into either a current or voltage, which may be outputted as an electrical signal. The plurality of detector elements may generate the signal indicative of an intensity of light incident on the detector element in series or in parallel. An intensity of the signal received by the detector elements of detector array 74 may be indicative of hemodynamic function, such as oxygen saturation of blood or the blood pressure of patient 12.

Processor 60 may receive the signals generated by the detector elements, either directly or indirectly (e.g., optical perfusion sensor 22 may consolidate the signals from each of the individual detector elements into one or more consolidated signals). Processor 60 may then determine relative changes the blood oxygen saturation level of the blood proximate to blood perfusion sensor 22 or other hemodynamic characteristics of patient 12 based on the signals generated by the detector elements of detector array 70. In examples in which the detector elements of detector array 74 includes a photodiode, an electrical signal outputted by each detector element of the detector array 74 may be directly or inversely proportional to the amount of light (e.g., the intensity of light) incident on the photodiode.

Although not shown in FIG. 3, in some examples, optical perfusion sensor 22 may include one or more optical elements, such as one or more lenses that helps focus light emitted from red LED 70 and IR LED 72. For example, red LED 70 and IR LED 72 may emit light through the one or more lenses, and detector array 74 may detect light received through one or more lenses, which may be the same as or different from the lenses through which red LED 70 and IR LED 72 emit light. In addition, in some examples, an optical barrier (not shown in FIG. 3) may be positioned to block direct transmission of light from LEDs 70, 72 to detector array 74. Red LED 70 may emit light in the red portion of the visible light spectrum, such as, but not limited to, light having a wavelength in a range of about 550 nanometers (nm) to about 750 nm. IR LED 72 may emit IR light in the IR portion of the light spectrum, such as, but not limited to, light having a wavelength in a range of about 750 nm to about 2.5 micrometers or greater.

Optical perfusion sensor 22 may be subcutaneously or submuscularly implanted within patient 12 such that LEDs 70, 72 and detector array 74 are oriented toward blood perfused tissue of patient 12. In the example of FIG. 3, red LED 70 and IR LED 72 are positioned on the same side of the blood perfused tissue as detector array 74, such that detector array 74 detects light emitted from LEDs 70, 72 and reflected by a blood mass within the tissue. This type of optical perfusion sensor may be referred to as a reflectance optical perfusion sensor or reflectance pulse oximeter.

Processor 60 controls optical perfusion sensor 22 to sense blood perfusion of tissue adjacent to red LED 70, IR LED 72, and detector array 74. Processor 60 may store electrical signals generated by detector array 74 of optical perfusion sensor 22 or perfusion values derived from the electrical signals generated by detector array 74 in memory 62. Processor 60 may control the operation of red LED 70 and IR LED 72. In some examples, processor 60 may control red LED 70 and IR LED 72 to sequentially emit light, such that only one of the LEDs 70, 72 emits light at a time.

Processor 60 may also control the operation of detector array 74. In some examples, processor 60 may determine an intensity of each wavelength of light emitted by the respective LED 70, 72 by controlling the detector elements of detector array 74 to sequentially sense light having the wavelength that was most recently emitted. The detector elements of detector array 74 may sense light in series or in parallel. When the detector elements sense light in parallel, processor 60 may receive an electrical signal from the detector elements substantially simultaneously, which may be received by processor 60 as one signal or a plurality of separate signals. In examples in which the detector elements of detector array 74 provide separate electrical signals to processor 60, processor 60 is determine which, if any, detector element is detecting the greatest intensity of light. This may enable processor 60 to selectively activate detector elements of detector array 74 in order to, for example conserve energy.

In other examples, in order to separate the signals indicative of the red light and IR light, processor 60 may demodulate the electrical signal received from the detector elements of detector array 74. Light sensed by the detector elements of detector array 74 may include information about the intensity of red light emitted by red LED 70 and reflected by blood, as well as the intensity of IR light emitted by IR LED 72 and reflected by blood.

EGM sensing module 64 is electrically coupled to electrodes 18, 20. Electrodes 18, may be coupled to a surface of outer housing 24 (FIG. 1) of IMD 14 or may be otherwise coupled to housing 24 of IMD 14, e.g., with the aid of one or more medical leads that extend from housing 24. In some examples in which electrodes 18, 20 are coupled to a surface of outer housing 24 of IMD 14, electrodes 18, 20 may be formed by housing 24 (e.g., by exposed portions of an electrically conductive housing) or may be attached to the outer surface of housing 24. Housing 24 may be any suitable housing that encloses some of the components of IMD 14. In some examples, housing 24 may be a hermetic housing that hermetically seals at least processor 60, memory 62, EGM sensing module 64, telemetry module 66, and power source 68.

EGM sensing module 64 receives signals from at least one of electrodes 18, 20 in order to monitor electrical activity of heart 32 of patient 12 (FIG. 2). In other examples, EGM sensing module 64 may be electrically coupled to more than two electrodes. In some examples, EGM sensing module 64 may include a channel that comprises an amplifier with a relatively wide-band. Signals from sensing electrodes 18, 20 may be coupled to the wide-band amplifier and provided to a multiplexer. Thereafter, the signals may be converted to multi-bit digital signals by an analog-to-digital converter for storage in memory 62 as an EGM. In some examples, the storage of such EGMs in memory 62 may be under the control of a direct memory access circuit.

In some examples, processor 60 may employ digital signal analysis techniques to characterize the digitized cardiac signals stored in memory 62 to detect and classify the patient's heart rhythm from the electrical signals. Processor 60 may detect and classify the heart rhythm of patient 12 by employing any of the numerous signal processing methodologies known in the art. In other examples, processor 60 may not analyze the stored EGM signals, and such processing may be done by another processor, such as a processor within external device 16 (FIG. 1), programmer 42 (FIG. 2) or another external computing device. In some examples, processor 60 may generate and store marker codes indicative of different cardiac episodes that EGM sensing module 64 detects, and store the marker codes in memory 62 and/or transmit the marker codes to external device 16 or another external computing device. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

Telemetry module 66 includes any suitable hardware, firmware, software or any combination thereof for communicating with another device, such as external device 16 (FIG. 1) or programmer 42 (FIG. 2). Under the control of processor 60, telemetry module 66 may receive downlink telemetry from and send uplink telemetry to external device 16 or programmer 42 with the aid of an antenna, which may be internal and/or external. Processor 60 may provide the data to be uplinked to external device 16 and the control signals for the telemetry circuit within telemetry module 66, e.g., via an address/data bus. In some examples, telemetry module 66 may provide received data to processor 60 via a multiplexer.

The various components of IMD 14 are coupled to power source 68, which may include a rechargeable or non-rechargeable battery. A non-rechargeable battery may be selected to last for several years, while a rechargeable battery may be inductively charged from an external device, e.g., on a daily or weekly basis.

The block diagram shown in FIG. 3 is merely one example of an IMD 14. In other examples, IMD 14 may include a fewer or greater number of components. For example, in examples in which IMD 14 is incorporated with a medical device that delivers therapy to patient 12, IMD 14 may also include a therapy delivery module, such as an electrical stimulation generator (e.g., a neurostimulator) or a fluid pump.

Optical perfusion sensor 22 and EGM sensing module 64 are shown to be separate from processor 60 in FIG. 3. In other examples, processor 60 may include the functionality attributed to optical perfusion sensor 22 and/or EGM sensing module 64 herein. For example, optical perfusion sensor 22 and EGM sensing module 64 shown in FIG. 3 may include software executed by processor 60. If optical perfusion sensor 22 or EGM sensing module 84 includes firmware or hardware, optical perfusion sensor 22 or EGM sensing module, respectively, may be a separate one of the one or more processors 60 or may be a part of a multifunction processor. As previously described, processor 60 may comprise one or more processors.

In some examples, some of the components of IMD 14 shown in the example of FIG. 3 may be relocated in another device. For example, optical perfusion sensor 22 may be enclosed in a separate housing from EGM sensing module 64 or other components of IMD 14. That is, although optical perfusion sensor 22 is shown in FIG. 3 to be incorporated within a housing of IMD 14 that also encloses other components, such as processor 60 and EGM sensing module 64, in other examples, optical perfusion sensor 22 may be enclosed in a separate housing as part of a separate optical perfusion sensor 22. An optical perfusion sensor 22 that is enclosed in a separate housing from the IMD 14 housing may be mechanically coupled to IMD 14 or may be mechanically decoupled from IMD 14. For example, in some examples, optical perfusion sensor 22 including red LED 70, IR LED 72, and detector array 74 may be implanted within patient 12 at a separate location from IMD 14. In such examples, optical perfusion sensor 22 may communicate with IMD 14 via a wired connection or via wireless communication techniques, such as RF telemetry.

In yet other examples, at least a part of optical perfusion sensor 22 may be external to patient 12. For example, optical perfusion sensor 22 may monitor the blood oxygen saturation level of tissue of patient 12 through an epidermis of patient (e.g., through skin on a finger, earlobe or forehead of patient 12). Optical perfusion sensor 22 may transmit the electrical signals generated by detector array 74 that are indicative of the sensed intensity of red light and IR light to another device, such as IMD 14, external device 16 or programmer 42. In some examples, data from at least one of optical perfusion sensor 22 or EGM sensing module 64 may be uploaded to a remote server, from which a clinician or another user may access the data to analyze the patient's condition. An example of a remote server is a server provided via the Medtronic CareLink® Network, available from Medtronic, Inc. of Minneapolis, Minn.

Figure 4:
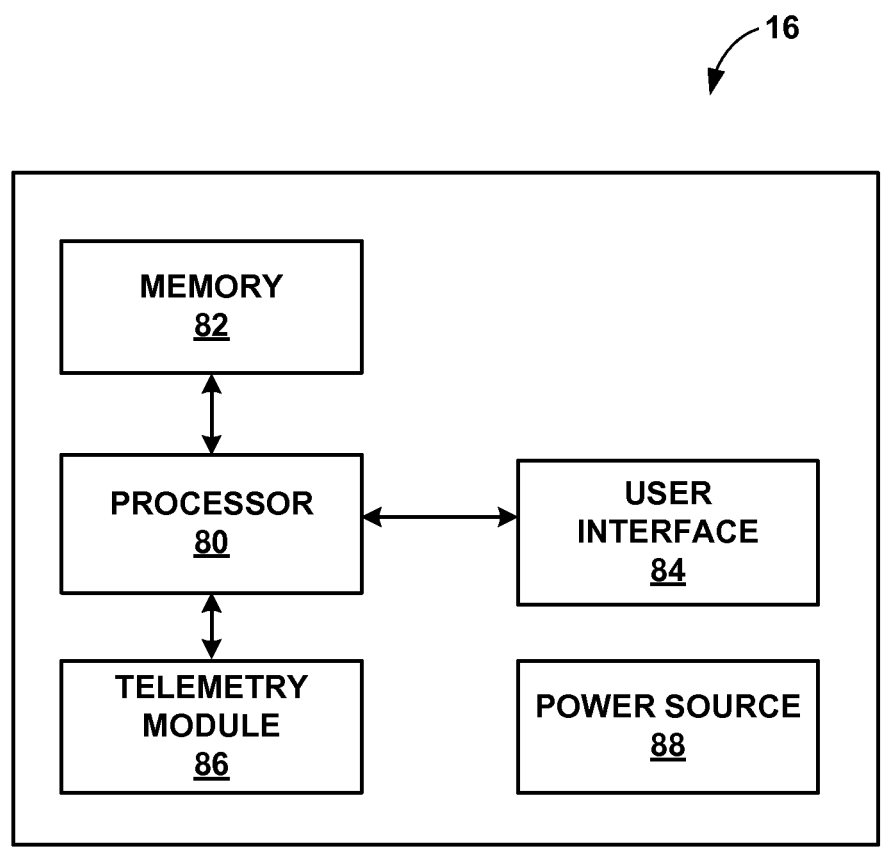
FIG. 4 is a functional block diagram of an example medical device programmer.

FIG. 4 is block diagram of an example external device 16. As shown in FIG. 4, external device 16 includes processor 80, memory 82, user interface 84, telemetry module 86, and power source 88. External device 16 may be a dedicated hardware device with dedicated software for interrogating IMD 14 to obtain information stored in memory 62 (FIG. 3), and, in some examples, for programming IMD 14. Alternatively, external device 16 may be an off-the-shelf computing device running an application that enables external device 16 to communicate with IMD 14.

A user may use external device 16 to modify the EGM and tissue perfusion sensing parameters of IMD 14. For example, the user may program the frequency at which EGM signals are sensed by EGM sensing module 64 (FIG. 3) or the tissue perfusion sensing time window for actively sensing changes in tissue perfusion with optical perfusion sensor 22. The clinician may interact with external device 16 via user interface 84, which may include display to present graphical user interface to a user, and a keypad or another mechanism for receiving input from a user.

Processor 80 can take the form of one or more microprocessors, DSPs, ASICs, FPGAs, programmable logic circuitry, or the like, and the functions attributed to processor 80 herein may be embodied as hardware, firmware, software or any combination thereof. Memory 82 may store instructions that cause processor 80 to provide the functionality ascribed to external device 16 herein, and information used by processor 80 to provide the functionality ascribed to external device 16 herein. Memory 82 may include any fixed or removable magnetic, optical, or electrical media, such as RAM, ROM, CD-ROM, hard or floppy magnetic disks, EEPROM, flash memory or the like. Memory 82 may also include a removable memory portion that may be used to provide memory updates or increases in memory capacities. A removable memory may also allow patient data to be easily transferred to another computing device, or to be removed before external device 16 is used to program therapy for another patient.

External device 16 may communicate wirelessly with IMD 14, e.g., using RF communication or proximal inductive interaction. This wireless communication is possible through the use of telemetry module 86, which may be coupled to an internal antenna or an external antenna. An external antenna that is coupled to external device 16 may correspond to the programming head that may be placed over the implant site of IMD 14, as described above with reference to FIG. 1. Telemetry module 86 may be similar to telemetry module 66 of IMD 14 (FIG. 3).

Telemetry module 86 may also be configured to communicate with another computing device via wireless communication techniques, or direct communication through a wired connection. Examples of local wireless communication techniques that may be employed to facilitate communication between external device 16 and another computing device include RF communication according to the 802.11 or Bluetooth specification sets, infrared communication, e.g., according to the IrDA standard, or other standard or proprietary telemetry protocols. In this manner, other external devices may be capable of communicating with external device 16 without needing to establish a secure wireless connection.

Power source 88 delivers operating power to the components of external device 16. Power source 88 may include a battery and a power generation circuit to produce the operating power. In some embodiments, the battery may be rechargeable to allow extended operation. Recharging may be accomplished by electrically coupling power source 88 to a cradle or plug that is connected to an alternating current (AC) outlet. In addition or alternatively, recharging may be accomplished through proximal inductive interaction between an external charger and an inductive charging coil within external device 16. In other embodiments, traditional batteries (e.g., nickel cadmium or lithium ion batteries) may be used. In addition, external device 16 may be directly coupled to an alternating current outlet to power external device 16. Power source 88 may include circuitry to monitor power remaining within a battery. In this manner, user interface 84 may provide a current battery level indicator or low battery level indicator when the battery needs to be replaced or recharged. In some cases, power source 88 may be capable of estimating the remaining time of operation using the current battery.

Figure 5A:
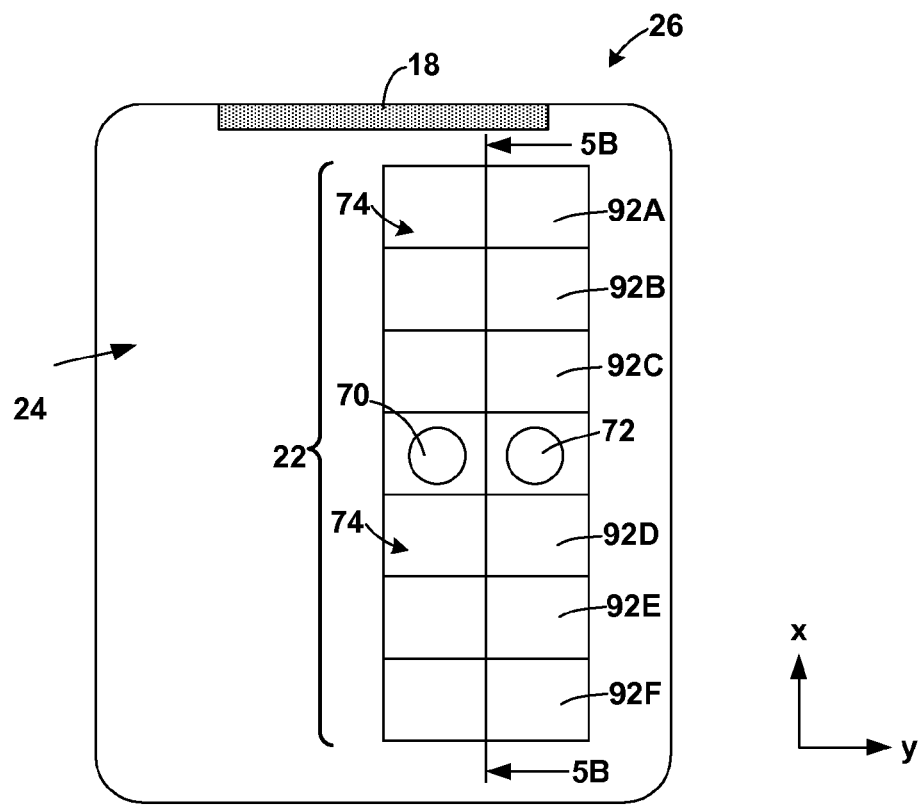
FIG. 5A is a conceptual illustration of a header of an IMD, which includes an optical perfusion sensor including a nonplanar detector array.
Figure 5B:
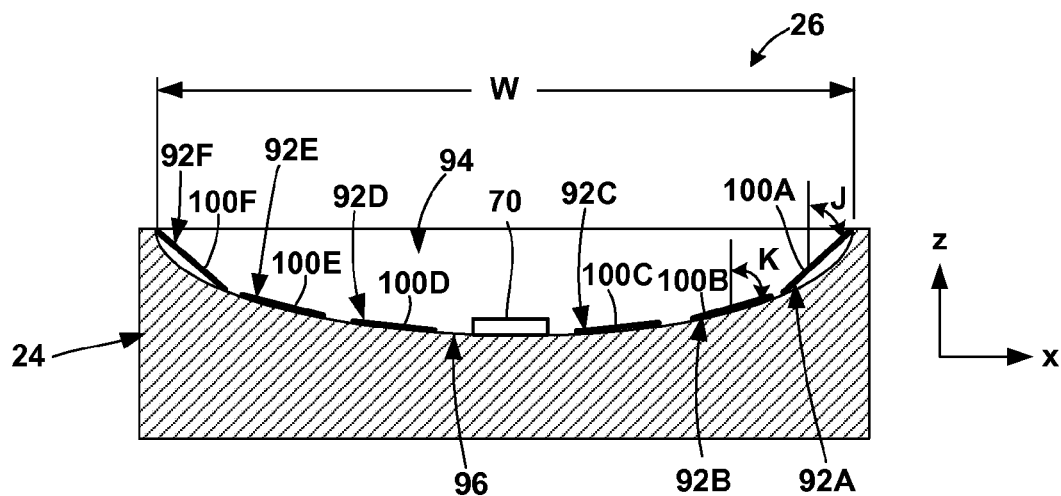
FIG. 5B is a conceptual partial cross-sectional view of the optical perfusion sensor shown in FIG. 5A.

FIG. 5A is a conceptual illustration of an example of header 26 of IMD 14. FIG. 5B is a conceptual cross-sectional illustration of header 26 of IMD 14 taken along line 5B-5B in FIG. 5A. In some examples, header 26 may be formed from plastic, although other materials (e.g., titanium) are also contemplated. Although FIG. 5B (as well as FIGS. 7A-7B) illustrates header 26 as being substantially solid, in other examples, header 26 may include other components. That is, housing 24 of IMD 14 may enclose electronic components or other components within header 26.

As shown in FIG. 5A, header 26 may include electrode 18 that may be used to sense cardiac signals of heart 32 (FIG. 2) of patient 12. Electrode 18 may be located on an outer surface of housing 24 of IMD 14 or housing 24 may define a recess configured to at least partially receive electrode 18.

Figure 6:
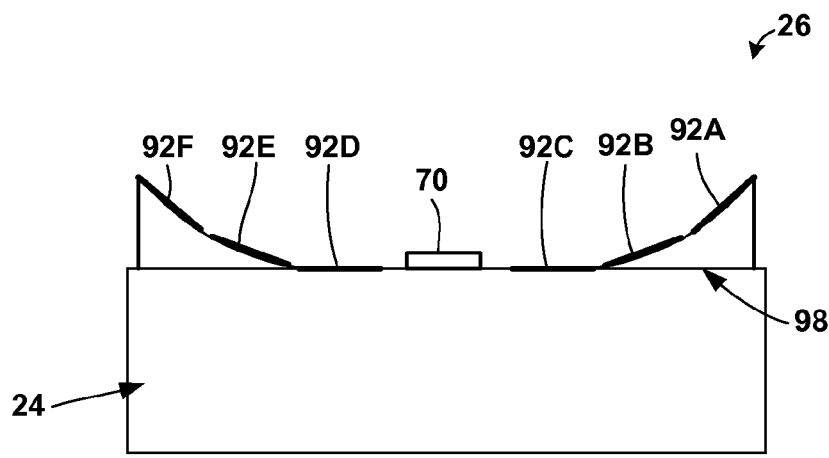
FIGS. 6, 7A and 7B are conceptual cross-sectional views of examples of optical perfusion sensors that include nonplanar detector arrays.

Optical perfusion sensor 22 may also be incorporated within or otherwise coupled to header 26. In the example shown in FIGS. 5A-5B, optical perfusion sensor 22 includes red LED 70, IR LED 72, and detector array 74, which includes a plurality of detector elements 92A-92F. In some examples, detector elements 92A-92F may be symmetrically arranged about red LED 70 and IR LED 72 in at least one plane (e.g., in the x-z plane, where orthogonal x-y-z axes are shown in FIGS. 5A-5B for ease of description only). Although six detector elements 92A-92F are shown in FIGS. 5A-6, in other examples, detector array 74 may include any suitable number of detector elements, such as greater than or less than six detector elements. In the example shown in FIG. 5A, detector elements 92A-92F and red LED 70 and IR LED 72 have fixed positions relative to each other, such that detector elements 92A-92F, red LED 70, and IR LED 72 do not move relative to each other.

Detector elements 92A-92F may each generate a signal indicative of an intensity of light incident on the respective detector element. For example, at least some of the detector elements 92A-92F of detector array 74 may include a photodiode that converts light into either a current or voltage. In other examples, detector elements 92A-92F may include any suitable photodetector. In some examples, signals from different detector elements 92A-92F may be weighted according to their respective positions. For example, the electrical signals from detector elements 92A-92F may be weighted to generate a weighted average intensity or a summation of intensity values to generate an overall signal value for detector array 74.

In some examples, at least two detector elements 92A-92F may be sensitive to different wavelengths of light. Red LED 70, IR LED 72, and detector elements 92A-92F may be directly or indirectly electrically coupled to electronics within housing 24 of IMD 14. For example, hermetic feedthroughs may electrically couple red LED 70, IR LED 72, and each of the detector elements 92A-92F directly or indirectly to processor 60 of IMD 14 (FIG. 3).

Red LED 70, IR LED 72, and detector elements 92A-92F are positioned on a common side of housing 24 of IMD 14, such that detector elements 92A-92F may detect light that is emitted by red LED 70 and IR LED 72 and reflected by blood of patient 12 proximate to optical perfusion sensor 22. In the example shown in FIGS. 5A-5B, outer housing 24 of IMD 14 defines recess 94 in header 26. Red LED 70, IR LED 72, and detector elements 92A-92F are disposed within recess 94, such that red LED 70, IR LED 72, and detector elements 92A-92F do not protrude from recess 94. For example, red LED 70, IR LED 72, and detector elements 92A-92F may be coupled to surface 96 within recess 94 using any suitable technique, such as an adhesive, welding (e.g., ultrasonic welding), interlocking parts, and the like. In the example shown in FIG. 5A, surface 96 has a curvilinear profile, and, in some examples, may have a parabolic profile (e.g., in cross-section). In some examples, an adhesive or other material may fill a space between wall 96 and the detector elements 92A-92F. In some examples, an epoxy or another material may be positioned within recess 94 to at least partially fill recess 94 (e.g., at least partially covering red LED 70, IR LED 72 and detector elements 92A-92F) to help minimize the risk of tissue trauma and tissue ingrowth that may affect the sensitivity of optical perfusion sensor 22.

In other examples of IMD 14, red LED 70, IR LED 72, and detector elements 92A-92F may protrude at least partially from outer housing 24 of IMD 14. An example of a header including red LED 70, IR LED 72, and detector elements 92A-92F positioned on an outer surface 98 of housing 24 and protruding from an outer surface 98 of housing 24 is shown in FIG. 6.

Returning now to FIGS. 5A and 5B, detector elements 92A-92F are arranged in a nonplanar configuration. That is, as shown in FIG. 5B, detector elements 92A-92F are arranged in a 3D array, such that at least some of detector elements 92A-92F of detector array 74 have different spatial positions in at least three different dimensions. For example, at least some of detector elements 92A-92F may have different positions along the x-axis, y-axis, and z-axis directions.

In the example shown in FIGS. 5A and 5B, at least some of detector elements 92A-92F are located at different distances in at least two different dimensions relative to red LED 70 and IR LED 72. For example, at least some of detector elements 92A-92F may be positioned at different elevations (e.g., measured substantially along a z-axis direction) relative to red LED 70 and IR LED 72. As an example, detector elements 92A and 92C have a different elevation relative to red LED 70 and IR LED 72. Although red LED 70 and IR LED 72 are shown in FIGS. 5A and 5B to have the same elevation, in other examples, red LED 70 and IR LED 72 may have different elevations (e.g., measured along the z-axis direction), such that one of the LEDs 70, 72 is closer to tissue (which maybe proximate recess 94).

Detector elements 92A-92F are also positioned to at least partially surround red LED 70 and IR LED 72, e.g., on at least two sides of red LED 70 and IR LED 72 as shown in FIGS. 5A and 5B. In addition, detector elements 92A-92F are positioned at different distances measured along the x-axis direction relative to red LED 70 and IR LED 72. For example, as shown in FIG. 5B, detector elements 92C and 92B are positioned different distances from IR LED 72. In the example shown in FIG. 5B, detector elements 92C, 92D are on opposite sides of red LED 70 and IR LED 72, and positioned at substantially equal distances in at least two dimensions (e.g., the z-axis and x-axis directions) from red LED 70 and IR LED 72. In addition, in the example shown in FIG. 5B, detector elements 92B, 92E are on opposite sides of red LED 70 and IR LED 72, and positioned at substantially equal distances in at least two dimensions (e.g., the z-axis and x-axis directions) from red LED 70 and IR LED 72. In FIG. 5B, detector elements 92A, 92F are on opposite sides of red LED 70 and IR LED 72, and positioned at substantially equal distances in at least two dimensions (e.g., the z-axis and x-axis directions) from red LED 70 and IR LED 72.

In other examples, detector elements 92A-92F may have other arrangements relative to red LED 70 and IR LED 72. However, in the examples described herein, at least two detector elements 92A-92F are positioned on opposite sides of at least one of red LED 70 or IR LED 72, and at least two detector elements 92A-92F are positioned different distances from at least one of red LED 70 or IR LED 72.

Positioning at least two detector elements 92A-92F to at least partially surround red LED 70 and IR LED 72 and at different positions in at least two different dimensions relative to red LED 70 and IR LED 72 may help increase the probability that detector array 74 senses light that was reflected by blood of patient 12, such as light that was reflected by blood in a blood vessel or other vasculature of patient 12. Detector elements 92A-92F of detector array 74 may partially surround red LED 70 and IR LED 72. In other examples, as described in further detail with respect to FIG. 8A, detector elements 92A-92F may substantially surround red LED 70 and IR LED 72, e.g., by forming a substantially annular configuration around red LED 70 and IR LED 72.

In order to more accurately and precisely determine hemodynamic characteristics of patient 12, it may be desirable for the light incident on detector elements 92A-92F of detector array 74 to travel through at least one blood vessel (e.g., an artery), and, in some cases, through multiple blood vessels or other vasculature of the patient. When a clinician implants IMD 14 in patient 12, the clinician may implant monitor 14 such that optical perfusion sensor 22 is proximate to vasculature of patient 12. Due to the inhomogeneity of the vasculature in patient, the movement of sensor 22 after implantation, and changes in the patient's tissue characteristics, however, the proximity of optical perfusion sensor 22 to vasculature may change after implantation.

In some cases, if the relative position between optical perfusion sensor 22 and vasculature changes, the amount of light incident on detector array 74 that has been reflected by blood in vasculature of patient 12 may change, thereby possibility decreasing the sensitivity of optical perfusion sensor 22. Diversifying the position of detector elements 92A-92F of detector array 92 relative to the blood-perfused tissue that may be adjacent to optical perfusion sensor 22 (through which red LED 70 and IR LED 70 emit light) may help reduce sensitivity decreases attributable to changes in the position of optical perfusion sensor 22 relative to vasculature of patient 12. Placement of multiple detector elements 92A-92F, as well as multiple detector elements 92A-92F in a 3D array and/or to at least partially surround red LED 70 and IR LED 72 with detector elements may increase the probability of receiving light reflected by blood. The arrangement of detector elements 92A-92F may also help optical perfusion sensor 22 sense tissue perfusion within a larger region of tissue compared to an optical perfusion sensor including a single detector element.

The position of detector elements 92A-92F relative to each other may affect the amount of light that is sensed by detector array 74, and, therefore, the sensitivity of optical perfusion sensor 22 to changes in the hemodynamic characteristics of patient 12, such as the blood oxygen saturation level. Due to the optical scattering properties of biological tissue, light emitted by red LED 70 and IR LED 72 may be diffused upon entrance into the blood-perfused tissue proximate to optical perfusion sensor 22. The scattered light emitted by red LED 70 and IR LED 72 may be reflected by blood, which may be reflected at various angles. Thus, the reflected light that is incident on detector array 74 may have various angles of incidence. Diversifying the location and orientation of detector elements 92A-92F by positioning detector elements 92A-92F in a nonplanar configuration may help increase the amount of reflected light that is incident on detector array 74, which may increase the sensitivity of optical perfusion sensor 22.

In addition, at least partially surrounding red LED 70 and IR LED 72 with detector elements 92A-92F may help increase the possibility that detector array 74 senses light emitted by red LED 70 and IR LED 72 that is reflected by blood of patient. Again, due to the optical scattering properties of biological tissue, the light emitted by red LED 70 and IR LED 72 may be reflected back to optical perfusion sensor 22 in a non-uniform and substantially unpredictable manner. If optical perfusion sensor 22 included a single detector element, the single detector element would only sense a small percentage of light emitted by red LED 70 and IR LED 72 and reflected back to optical perfusion sensor 22 by the blood-perfused tissue. Furthermore, the small percentage of light incident on a single detector may only indicate the blood oxygen levels of the blood within a small sample of tissue.

Increasing the number of detector elements may help increase the quantity (or amount) of light incident on optical perfusion sensor 22 that is detected by detector array 74. In general, this may help increase the sensitivity of optical perfusion sensor 22 to changes in blood oxygen saturation levels of patient 12. In addition, collecting more reflected light by increasing the number of plurality of detector elements may help optical perfusion sensor 22 monitor the blood oxygen levels of a larger volume (e.g., a larger sample) of tissue. That is, because more reflected light is captured by detector array 74 including a plurality of detector elements, the probability detecting light that has reflected off of blood in different regions of tissue (e.g., in different blood vessels or different parts of the same blood vessel) may increase. This may help generate a better indication of the patient's blood oxygen saturation levels by increasing the quantity of light reflected light that is received by detector array 74 and/or increasing the volume of tissue that is sample by optical perfusion sensor 22. More tissue sites and a larger volume of tissue are sampled by optical perfusion sensor 22 as a result of collecting more light that is reflected by blood within the tissue, and, therefore, optical perfusion sensor 22 may observe the blood characteristics within a larger sample of tissue.

Placing detector elements 92A-92F along a nonplanar surface 96 may help increase a detector surface area while minimizing the projected size of optical perfusion sensor 22 in at least one dimension. For example, as shown in FIGS. 5A and 5B, positioning detector elements 92A-92F along a nonplanar surface 96 may help increase a detector surface area while minimizing a width W of optical perfusion sensor 22 compared to an arrangement in which detector elements 92A-92F are positioned along a planar surface. Minimizing at least one dimension of optical perfusion sensor 22 may be useful for providing a minimally invasive IMD 14.

Each of the detector elements 92A-92F includes at least one photodetection surface 100A-100F, respectively. The photodetection surfaces 100A, 100B of detector elements 92A, 92B, respectively, may be substantially planar, although other profiles (e.g., curvilinear) are contemplated. Detector elements 92A-92F may sense light incident on the respective photodetection surface 100A-100F. In the example shown in FIGS. 5A and 5B, the photodetection surface of at least two of the detector elements 92A-92F are not parallel, e.g., oriented at different angles relative to each other. For example, the photodetection surfaces 100A, 100B of detector elements 92A, 92B, respectively, may be oriented at different angles relative to photodetection surface 100C of detector element 92C. In the example shown in FIG. 5B, photodetection surface 100A of detector element 92A is oriented at an angle J relative to a reference line that is substantially perpendicular to a major surface of photodetection surface 100C of detector element 92C, or, in some examples, relative to an axis that is substantially perpendicular to an emitter surface of red LED 70. Photodetection surface 100B of detector element 92B is oriented at an angle K relative to a reference line that is substantially perpendicular to a major surface of photodetection surface 100C of detector element 92C, or, in some examples, relative to an axis that is substantially perpendicular to an emitter surface of red LED 70. In the example shown in FIG. 5B, angles J and K are different. Angles J and K may be any suitable angle.

Orienting two or more detector elements 92A-92F at different angles relative to each other may help increase the probability that detector array 74 senses light that was transmitted through blood-perfused tissue, and, in some cases, may increase the probability that detector array 74 senses light that was transmitted through vasculature of patient 12. Light incident on one of the detector elements 92A-92F may not be incident on a different one of the detector elements 92A-92F due to the different orientations of the respective photodetection surfaces relative to the blood-perfused tissue.

Blood-perfused tissue adjacent housing 24 of IMD 14 may scatter the light emitted by red LED 70 and IR LED 72, such that light that is reflected by the blood-perfused tissue and sensed by detector array 74 may have varying angles of incidence on photodetection surfaces 100A-100F of detector elements 92A-92F, respectively. Accordingly, selecting different angles of orientation for photodetection surfaces 100A-100F of detector elements 92A-92F may help diversify the angles at which detector array 74 may capture light that is reflected by the blood-perfused tissue, thereby increasing the possibility that detector array 74 senses light.

In other examples of optical perfusion sensor 22, optical perfusion sensor 22 may be coupled to case 28 of IMD 14, rather than header 26. In FIGS. 5A and 5B, as well as FIG. 6, the detector elements 92A-92F are arranged in a substantially curvilinear surface 96, which is concave in FIGS. 5B and 6. In other examples, the curvilinear surface 96 may be substantially convex. The curvilinear surface may help focus stray light onto at least one of the photodetection surface 100A-100F of detector elements 92A-92F, respectively. For example, the surface 96 defined within recess 94 of housing 24 may create a mirroring effect that reflects light onto one of the photodetection surfaces 100A-100F. In some examples, the surface 96 within recess 94 may be coated with an optical material to increase the reflective properties of surface 96. While the detector elements 92A-92F are positioned on a surface 96 defined by housing 24, in other examples, detector elements 92A-92F may be indirectly coupled to housing 24. For example, detector elements 92A-92F may be arranged to define a 3D array on a member separate from housing 24, and the member may then be coupled to the housing 24.

Figure 7A:
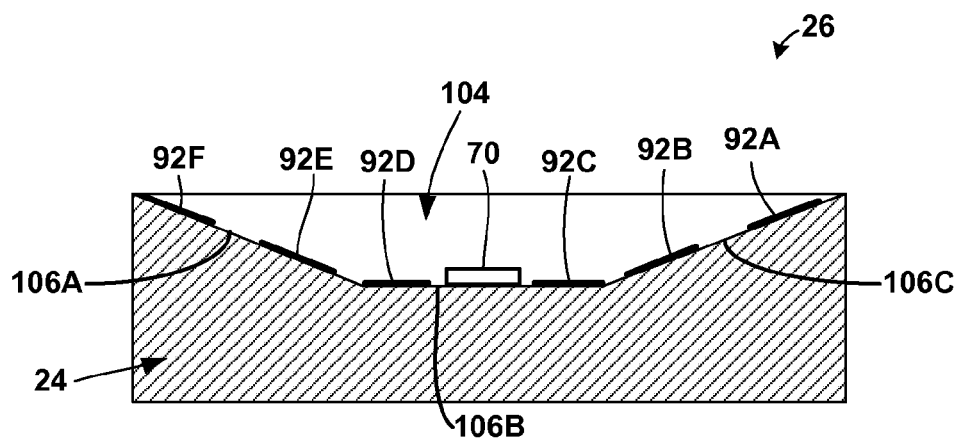
Figure 7B:
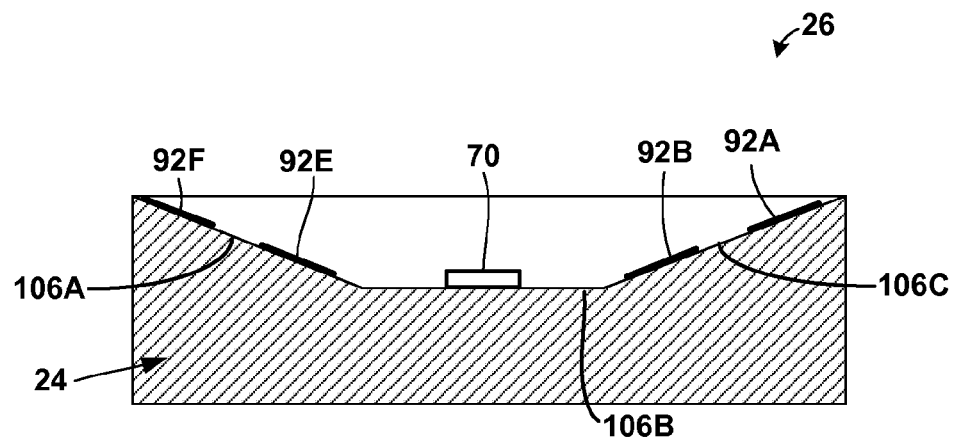

In other examples, detector elements 92A-92F may be coupled to more than one discontinuous surface defined by housing 24 (or another member), which may or may not each be curvilinear. The discontinuous surfaces may be arranged relative to each other to define a nonplanar (e.g., 3D) array when at least one of the detector elements 92A-92F are positioned on the surfaces. FIGS. 7A and 7B are conceptual partial cross-sectional views of other examples header 26 of IMD 14, which include a plurality of detector elements arranged on more than one discontinuous surface.

In FIG. 7A, housing 24 of IMD 14 defines recess 104 that includes at least three discontinuous surfaces 106A-106C on which detector elements 92A-92F are positioned. In other examples, recess 104 may include any suitable number of discontinuous surfaces. Surfaces 106A-106C may be arranged such that detector elements 92A-92F define a 3D array when detector elements 92A-92F are positioned within recess 104. In the example shown in FIG. 7A, detector elements 92A, 92B are positioned on surface 106C, detector elements 92C, 92D are positioned on surface 106B, and detector elements 92E, 92F are positioned on a different surface 106C. While red LED 70 and IR LED 72 are positioned on a common surface 106B of housing 24 with detector elements 92C, 92D, in other examples, as shown in FIG. 7B, red LED 70 and IR LED 72 may be positioned on a surface that does not include detector elements.

Figure 8A:
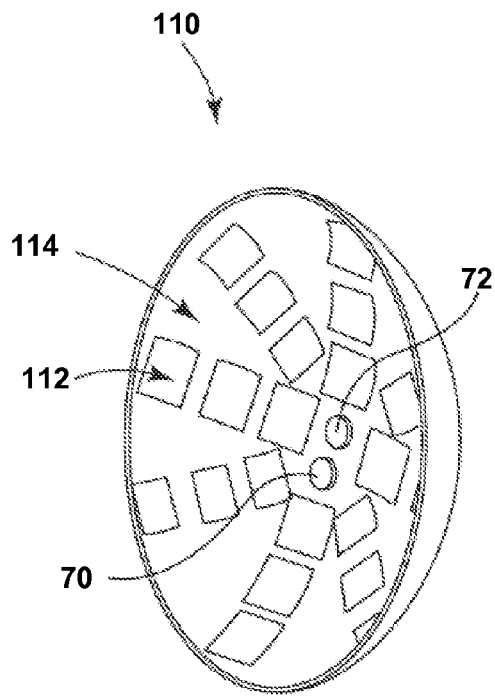
FIGS. 8A and 8B are conceptual perspective views of examples of an optical perfusion sensor that includes a nonplanar detector array.

FIG. 8A is a conceptual perspective view of another example optical perfusion sensor 110, which includes red LED 70, IR LED 72, and a detector array including a plurality of detector elements 112. Sensor 110 may be coupled to header 26 or case 28 of IMD 14 (FIG. 14). Detector elements 112 may each be similar to detector elements 92A-92F of detector array 74 (FIGS. 5A-5B). For example, detector elements 112 may each be any suitable photodetector, such as a photodiode. Although 24 detector elements 112 are shown in the example in FIG. 8A, in other examples, optical perfusion sensor 110 may include any suitable number of detector elements 112.

In the example shown in FIG. 8A, detector elements 112 are coupled to curvilinear surface 114, which may be defined by housing 24 of IMD 14 or another member. For example, housing 24 may define a recess including surface 114 or surface 114 may protrude from outer surface 98 (FIG. 6) of housing 24. As another example, a member separate from housing 24 may define surface 114 and the member may then be coupled to housing 24. In some examples, surface 114 may be parabola-shaped in cross-section or may define any suitable curvature in cross-section. Just as with the curvilinear surface 96 of recess 94 (FIG. 5B), due to its profile, curvilinear surface 114 may help focus stray light onto photodetection surfaces of detector elements 112. In some examples, curvilinear surface 114 may include an optical material to help reflect stray light onto the photodetection surfaces of detector elements 112.

Detector elements 112 are positioned on at least two sides of red LED 70 and IR LED 72. More particularly, detector elements 112 substantially surround red LED 70 and IR LED 72 in an annular configuration. In the example shown in FIG. 8A, detector elements 112 are symmetrically arranged in at least three dimensions about red LED 70 and IR LED 72. In other examples, detector elements 112 may not be symmetrically arranged about red LED 70 and IR LED 72. In some examples, at least one detector element 112 may be positioned between red LED 70 and IR LED 72.

In addition, in the example shown in FIG. 8A, detector elements 112 are arranged in a substantially nonplanar configuration. In particular, detector elements 112 are arranged in on a curvilinear surface, such that the detector array comprising detector elements 112 defines a curvilinear profile and detector elements 112 define a 3D array. In some examples, detector elements 112 are arranged in a 3D concave, bowl-like or dish-like configuration, which may or may not have a cross-sectional shape defined by a parabola. Nonplanar detector array 74 shown in FIGS. 5A and 5B also includes a curvilinear profile in cross-section. However, in contrast to detector elements 112, detector elements 92A-92F of detector array 74 are arranged to define a section of a 3D bowl-like configuration.

Just as with detector array 74 of FIGS. 5A and 5B, varying the position of detector elements 112 relative to each other and relative to red LED 70 and IR LED 72 in at least two dimensions may help increase the probability that the detector array of optical perfusion sensor 110 senses light that was reflected by blood in vasculature of patient 12. At least some of the detector elements 112 are oriented at different angles relative to each other, which may also help increase the probability that the detector array of optical perfusion sensor 110 senses light that was reflected by tissue.

Figure 8B:
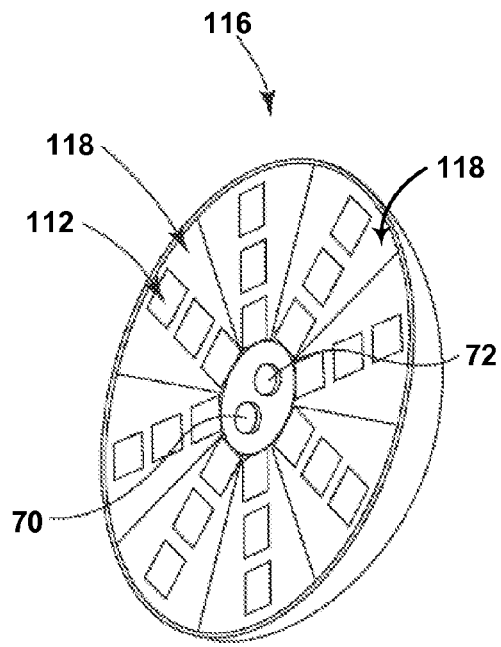

FIG. 8B is a conceptual perspective view of another example optical perfusion sensor 116, which includes red LED 70, IR LED 72, and a detector array including a plurality of detector elements 112. Optical perfusion sensor 116 is similar to sensor 110 of FIG. 8A. However, in this example, detector elements 112 are positioned on substantially planar surface 118. In some examples in which detector elements 112 are substantially planar, detector elements 112 may be more securely coupled to planar surfaces 118 compared to curvilinear surface 114 (FIG. 8A).

Planar surfaces 118 are arranged to define a generally concave space in which detector elements 112 are positioned to define a detector array having a nonplanar configuration. That is, planar surfaces 118 are nonparallel, such that detector elements 112 positioned on planar surfaces 118 define a 3D detector array. In the example shown in FIG. 8B, each planar surface 118 includes one column detector element 112 that extends away from red LED 70 and IR LED 72. Although eight planar surfaces 118 are shown in FIG. 8B, in other examples, optical perfusion sensor 116 may include any suitable number of planar surfaces, such as greater than or less than eight surfaces. Furthermore, a planar surface 118 may include more than one column of detector elements 112.

Although detector elements 112 are arranged in a substantially nonplanar profile, e.g., a 3D array, in the example of FIGS. 8A and 8B, in other examples, an optical perfusion sensor may include a plurality of detector elements arranged in a substantially 2D array. As described above, in a 2D array, at least some of the detector elements 112 may share a spatial position in one dimension, but have different spatial positions in at least two dimensions. For example, at least some of the detector elements 112 may lie in a common plane. As an example, detector elements 112 may be arranged in a single row along a parabolic or other curvilinear cross-section of the rounded surface 114. In some examples, the detector elements of the 2D array may at least partially surround one or more light sources, as shown in FIGS. 9A-9B.

Figure 9A:
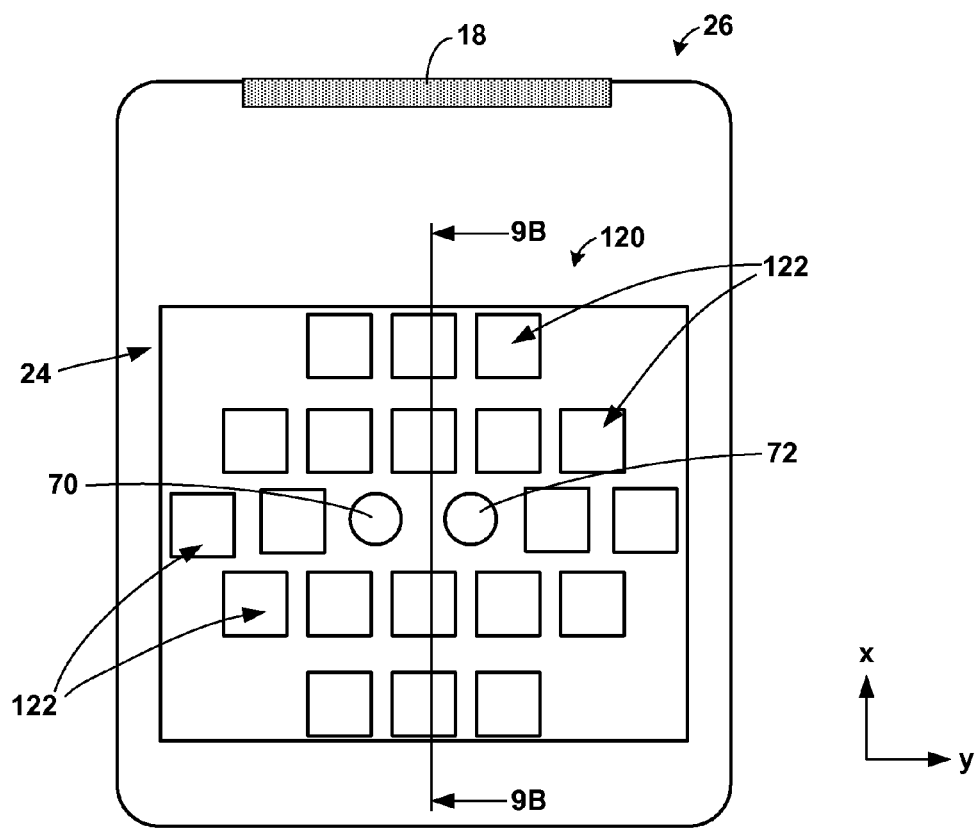
FIG. 9A is a conceptual illustration of a portion of an IMD, which includes an optical perfusion sensor including a substantially planar detector array.

FIG. 9A is a conceptual plan view of another example of an optical perfusion sensor 120, which may be incorporated into header 26 or case 28 of IMD 14 (FIG. 1), as shown in FIG. 9A, or in another implantable or external medical device. FIG. 9B is a conceptual cross-sectional illustration of optical perfusion sensor 120 that is taken along line 9B-9B in FIG. 9A. As with optical perfusion sensor 22, optical perfusion sensor 120 may be recessed in outer housing 24 of IMD 14, may protrude at least partially from an outer surface 98 (FIG. 6) of housing 24 or may be positioned on an outer surface 98 of housing. Optical perfusion sensor 120 includes red LED 70, IR LED 72, and a detector array including a plurality of detector elements 122. Red LED 70, IR LED 72, and detector elements 122 may be coupled directly or indirectly to housing 24. Although 20 detector elements 122 are shown in FIG. 9A, in other examples, optical perfusion sensor 120 may include any suitable number of detector elements.

Figure 9B:
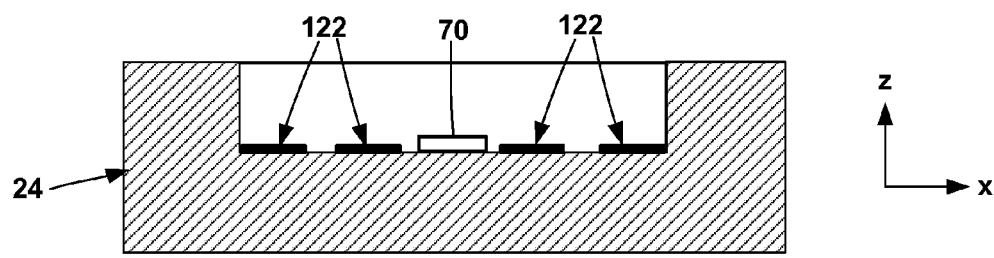
FIG. 9B is a conceptual cross-sectional view of the portion of the IMD shown in FIG. 9A.

In the example shown in FIGS. 9A and 9B, detector elements 122 are positioned on a common surface with red LED 70 and IR LED 72. The common surface may be, for example, substantially planar, such that detector elements 122, red LED 70, and IR LED 72 substantially lie within a common plane. In contrast, in the nonplanar detector arrays described with respect to FIGS. 5A-8, at least some of the detector elements lie in a different plane than red LED 70 and IR LED 72. In some examples, detector elements 122 are each disposed in separate openings within housing 24 of IMD 14.

Detector elements 122 are arranged in a substantially 2D array, which may be, but need not be, a planar configuration. In a 2D array of detector elements 122, the detector elements 122 have different spatial positions in at least two-dimensions. For example, in the example shown in FIGS. 9A and 9B, detector elements 122 share position along the z-axis, such that detector elements 122 are in a planar configuration. In addition, at least some of detector elements 122 have spatial positions along the x-axis and y-axis. However, at least some of the detector elements 122 share a spatial position along the x-axis or the y-axis. In other examples, optical perfusion sensor 22 may include a one dimensional (1D) detector array. A 1D detector array may include a plurality of detector elements in a linear arrangement, such that the detector elements share spatial positions in at least two dimensions. The detector elements of the 1D detector array may be positioned to at least partially surround red LED 70 and IR LED 72, e.g., by being positioned on opposite sides of red LED 70 and IR LED 72.

In the example shown in FIGS. 9A and 9B, detector elements 122 are arranged such that the photodetection surfaces of each of the detector elements 122 are substantially parallel. That is, unlike detector elements 92A-92F of detector array 74 (FIGS. 5A-5B) and detector elements 112 of the optical perfusion sensor 110 of FIG. 8A, detector elements 122 do not have different angular orientations. Instead, detector elements 12 have substantially similar angular orientations relative to red LED 70 and IR LED 72.

Detector elements 122 are positioned to substantially surround red LED 70 and IR LED 72 with detector elements 122, and, as shown in FIG. 9A, so as to define a substantially annular configuration around red LED 70 and IR LED 72. That is, at least some of the detector elements 122 are arranged in a concentric pattern around red LED 70 and IR LED 72, so as to define concentric rings around red LED 70 and IR LED 72. In other examples, detector elements 122 may be positioned on at least partially surround red LED 70 and IR LED 72 without defining a substantially annular configuration. For example, detector elements 122 may define a substantially quadrangular shape. In addition, in some examples (not shown in FIG. 9A or 9B), at least one detector element 122 may be positioned between red LED 70 and IR LED 72.

An optical perfusion sensor including detector elements 122 at various locations relative to red LED 70 and IR LED 72 may help increase the probability of receiving light reflected by blood in a blood vessel of a patient by increasing the volume of tissue that is observed by the optical perfusion sensor. As described above, increasing the volume of tissue that is observed by the optical perfusion sensor may increase a probability of receiving light that was reflected by blood in a blood vessel of patient 12. This may help provide a more accurate and precise reading of the blood oxygen saturation level of the patient's blood.

Figure 10A:
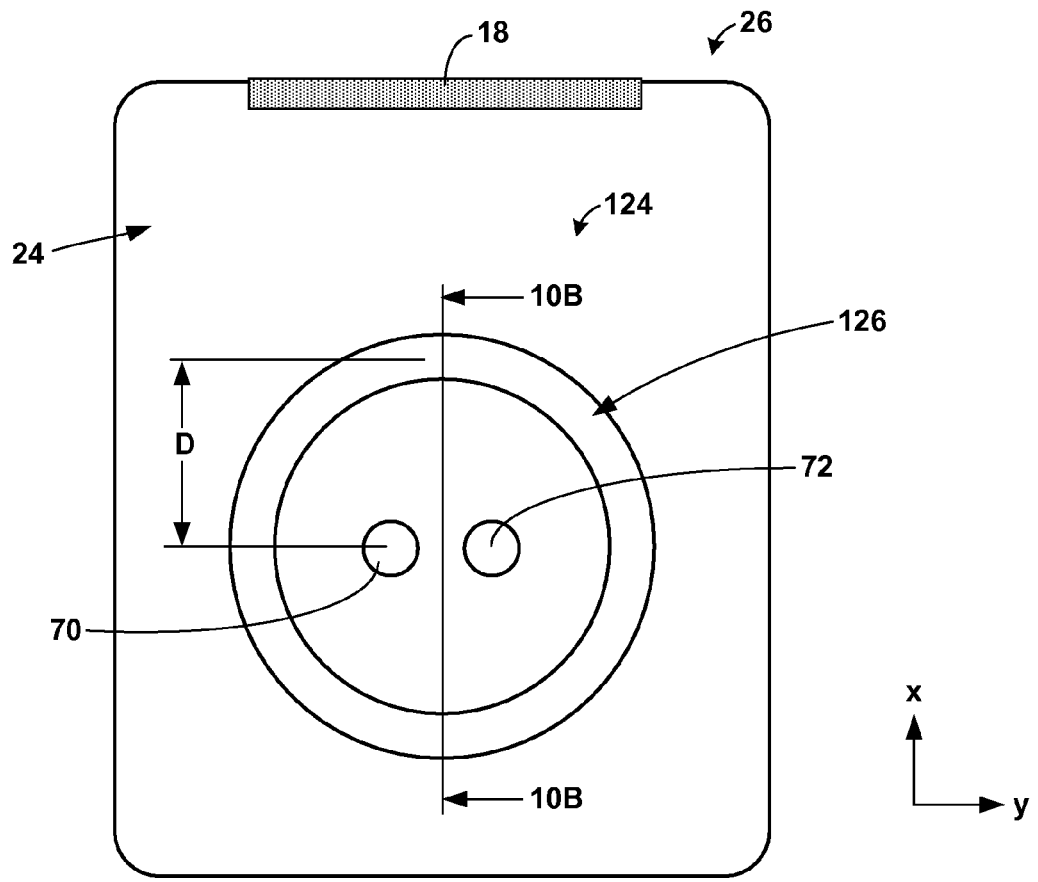
FIG. 10A is a conceptual illustration of a portion of an IMD, which includes an optical perfusion sensor including a detector that at least partially surrounds a light source.
Figure 10B:
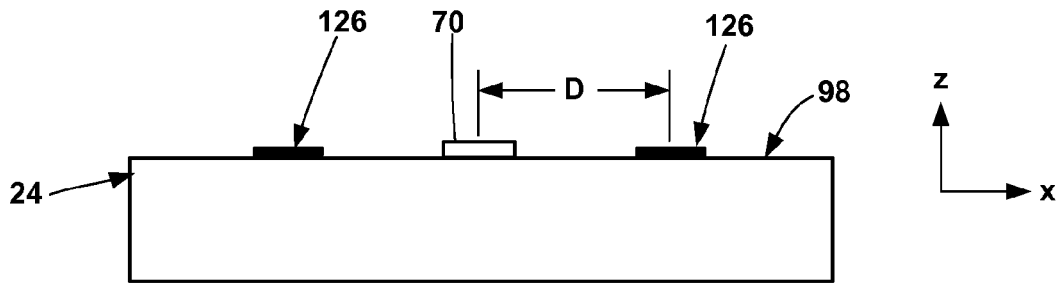
FIG. 10B is a conceptual cross-sectional view of the portion of the IMD shown in FIG. 10A.
Figure 11:
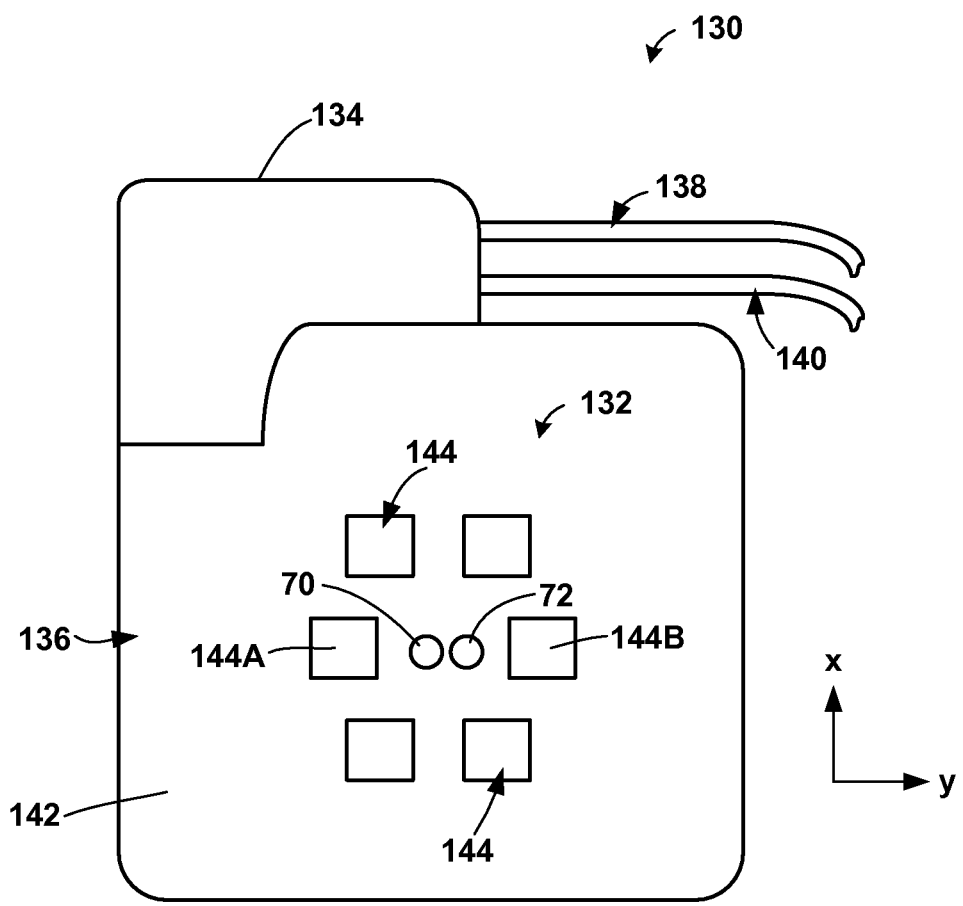
FIG. 11 is a conceptual illustration of another example of an implantable medical device that includes an optical perfusion sensor comprising a plurality of detector elements.

FIG. 10A is a conceptual plan view of another example of an optical perfusion sensor 124, which may be incorporated into header 26 or case 28 of IMD 14 (FIG. 1) as shown in FIG. 10A, or into a case or main body of IMD 14, IMD 34 (FIG. 2) or another implantable or external medical device, as described with respect to FIG. 11. FIG. 10B is a conceptual cross-sectional illustration of optical perfusion sensor 124 that is taken along line 10B-10B in FIG. 10A. In the example shown in FIGS. 10A and 10B, optical perfusion sensor 124 is positioned on outer surface 98 of housing 24. In other examples, optical perfusion sensor 124 may be at least partially recessed in outer housing 24 of IMD 14.

Optical perfusion sensor 124 includes red LED 70, IR LED 72, and an annular detector 126. Red LED 70, IR LED 72, and detector 126 may be coupled directly or indirectly to housing 24. Detector 126 may be similar to detector elements 92A-92F of detector array 74 (FIGS. 5A-5B). For example, detector 126 may comprise a photodetector that generates an electrical signal that varies as a function of an intensity of light incident on a photodetection surface of detector 126, which may generally face away from housing 24 such that detector 126 receives light emitted by red LED 70 and IR LED 72 and reflected by blood.

Detector 126 extends at least partially around of red LED 70 and IR LED 72. In the example shown in FIGS. 10A and 10B, detector 126 has a substantially continuous annular shape, such that detector 126 surrounds red LED 70 and IR LED 72 and is substantially symmetrically arranged around red LED 70 and IR LED 72. Detector 126 may include a single detector element or may include a plurality of detector elements defining a plurality of annular detector elements or defining one or more discontinuous annular detector arrays. For example, detector 126 may comprise a plurality of concentric detector elements or a plurality of detector elements that are positioned to define detector 126 that at least partially surrounds red LED 70 and IR LED 72. In some examples of optical perfusion sensor 124, as well as other examples of optical perfusion sensor 22 (FIGS. 5A-7B), optical perfusion sensor 110 (FIG. 8A), and detector array 120 (FIGS. 9A and 9B), the detector elements may be substantially equidistant from red LED 70 and IR LED 72.

In examples in which optical perfusion sensor 124 is used to monitor a hemodynamic characteristic of a patient, arranging detector 126 such that it extends around red LED 70 and IR LED 72 may help increase the probability of receiving light emitted by red LED 70 and IR LED 72 and diffused through tissue of the patient. In addition, compared to an optical perfusion sensor including a single detector element on one side of red LED 70 and IR LED 72, sensor 124 including detector element 126 located on at least two sides of red LED 70 and IR LED 72 may help increase the probability of receiving light reflected by blood in a blood vessel of patient 12 by increasing the volume of tissue that is observed by the optical perfusion sensor 126. In addition, as a result of detector 126 having a relatively large photodetection surface area that at least partially surrounds red LED 70 and IR LED 72, the sample size of blood-perfused tissue that is observed by optical perfusion sensor 124 may increase. This may help provide a more accurate and precise reading of the blood oxygen saturation level of the patient's blood.

In some cases, a distance between detector 126 and red LED 70 and IR LED 72 may affect the depth of tissue (measured substantially along a z-axis direction) sampled by light emitted by red LED 70 and IR LED 72 and detected by detector 126. In general, light emitted by red LED 70 and IR LED 72 and sensed by detector 126 may traverse through less tissue depth as the distance between detector 126 and red LED 70 and IR LED 72 decreases. Decreasing the tissue depth may decrease the probability of light being reflected by a blood mass. On the other hand, detector 126 may detect less light as the distance between detector 126 and red LED 70 and IR LED 72 increases due to the greater range of light scattering.

Detector 126 is spaced distance D from red LED 70 and IR LED 72. In the example shown in FIGS. 10A and 10B, distance D is measured from a center axis of red LED 70 or IR LED 72 and a center of detector 126, where the center is measured substantially along the x-y plane. In some examples, distance D may be in a range of about 2 millimeters (mm) to about 15 mm, such as about 3 mm to about 10 mm, in order to help maximize the amount of light emitted by red LED 70 and IR LED 72 and reflected by blood of patient 12 that detector 126 senses. However, other distances D are contemplated and may depend upon the size of red LED 70, IR LED 72 and detector 126. In other examples, detector 126 may be spaced distance D from a center axis of red LED 70 or IR LED 72, rather than both red LED 70 and IR LED 70.

Although an annular detector 126 is shown in FIGS. 10A and 10B, in other examples, detector 126 may have a partial annular shape or may be substantially non-annular (e.g., elliptical). For example, an outer perimeter of detector 126 may define a quadrilateral, a hexagon, octagon, and the like. In addition, although detector 126 is positioned on a planar surface 98 of housing 24, such that detector 126 is substantially planar, in other examples, detector 126 may be positioned on a nonplanar surface (e.g., surface 96 shown in FIG. 5B or surfaces 106A and 106C shown in FIGS. 7A and 7B).

FIG. 11 is a conceptual illustration of another example of IMD 130 that includes an optical perfusion sensor 132. IMD 130 includes header 134 and case 136. Case 136 may be hermetically sealed and may enclose various sensing and control circuitry for sensing one or more physiological parameters of patient 12, and, in some cases, a therapy delivery module for delivering therapy to patient 12 (e.g., electrical stimulation or a therapeutic agent). Header 134 provides a hermetically sealed passage for connecting therapy delivery elements 138, 140 to components within case 136. For example, if therapy delivery elements 138, 140 comprise leads with conductors, header 134 may electrically couple the conductors to components within case 136, e.g., with the aid of feed-through wires or connector pins. As another example, if therapy delivery elements 138, 140 comprise catheters that deliver a therapeutic agent to patient 12, header 134 may fluidically couple the catheters to a fluid reservoir within case 136. Therapy delivery elements 138, 140 are only partially shown in FIG. 11.

Optical perfusion sensor 132 includes red LED 70, IR LED 72, and a detector array comprising six detector elements 144. Although six detector elements 14 are shown in FIG. 11, in other examples, optical perfusion sensor 132 may include any suitable number of detector elements. In the example shown in FIG. 11, optical perfusion sensor 132 is coupled to side 142 of case 136. For example, red LED 70, IR LED 72, and each of the detector elements 144 may be disposed in one or more openings defined by an outer housing of case 136 or may be positioned on a top surface of the case 136 that does not define a recess. In other examples, sensor 132 may be coupled to one or more surfaces of header 134.

In FIG. 11, as well as the other figures, although red LED 70 and IR LED 72 are shown to have circular cross-sections and detector elements 144 are shown to have quadrilateral cross-sections, in other examples, red LED 70, IR LED 72, and detector elements may have any suitable shape. In the example shown in FIG. 11, detector elements 144 are positioned to surround red LED 70 and IR LED 72 to define a generally annular detector array. As with optical perfusion sensor 22 (FIGS. 5A-7B), varying the locations of detector elements 144 relative to red LED 70 and IR LED 72 may help increase the quantity of light that is detected by the detector array of optical perfusion sensor 132, which may help increase a signal to noise ratio. This may help optical perfusion sensor 132 generate a signal that provides a better indication of the blood oxygen saturation level of patient 12.

Detector elements 144 may be positioned to define a 2D array, whereby at least some of the detector elements 144 have different x-axis and y-axis positions (orthogonal x-y axes are shown in FIG. 11 for ease of description only) and have a common z-axis position (where the z-axis is substantially orthogonal to the plane of the image shown in FIG. 11). In other examples, detector elements 144 may be positioned to define a 3D array, whereby at least some of the detector elements 144 have different x-axis, y-axis, and z-axis positions. In addition, in other examples, detector elements may be positioned to define a substantially 1D array. For example, optical perfusion sensor 132 may only include detector elements 144A and 144B, which have substantially similar x-axis and z-axis positions, but have different y-axis positions. That is, detector elements 144A, 144B define a linear detector array. However, the linear detector array still at least partially surrounds red LED 70 and IR LED 72.

In some examples of optical perfusion sensors described herein, one or more lenses may be positioned over the one or more light sources (e.g., red LED 70 and IR LED 72) and/or one or more of the detector elements of a detector array (e.g., detector elements 92A-92F of detector array 74). A lens positioned over the one or more light sources may help to focus light that is emitted by the light source, and a lens positioned over one or more of the detector elements may help focus reflected light that originated from the one or more light sources. As described in U.S. Pat. No. 6,198,952 to Miesel, entitled, "MULTIPLE LENS OXYGEN SENSOR FOR MEDICAL ELECTRICAL LEAD," which issued on Mar. 6, 2001, and is incorporated herein by reference in its entirety, in some examples, a suitable lens may comprise a flat panel, cylinder or half-cylinder of glass, sapphire, ruby, quartz or another suitable light transmissive material.

In addition, an optical perfusion sensor described herein may include an optical barrier (or "light barrier") disposed between the one or more light sources and the detector elements of the detector array. As described in U.S. Pat. No. 6,198,952 to Miesel, an optical barrier may help prevent direct, reflected or refracted transmission of light that is not reflected by blood to be detected by a detector element. Light that is not reflected by blood and impinged on a detector element may result in an erroneous blood oxygen saturation level estimation because the detector element is typically unable to distinguish the origin of the light.

A reflectance optical perfusion sensor including a nonplanar (or 3D) detector array or a detector array that includes a plurality of detector elements that at least partially surround a light source may be formed using any suitable technique. In general, a light source may be coupled to a housing and a plurality of detector elements may be coupled to the housing to define the detector array. For example, the detector elements may be coupled to one or more surfaces of the housing, either directly or indirectly, to define a three-dimensional array. The detector array and the one or more light sources of the reflectance optical perfusion sensor may be positioned such that the detector elements sense light emitted by the one or more light sources and reflected back to the optical perfusion sensor by a blood mass. For example, the detector array and one or more light sources may be positioned on the same side of a housing of a medical device, which may be an implantable medical device.

Various examples of the invention have been described. These and other examples are within the scope of the following claims.

The invention claimed is:

1. An implantable medical device comprising:
an outer housing surface including a first portion configured having a planar profile and a second portion of the surface configured having a curvilinear profile;
a light source disposed on the first portion having an emitter surface oriented in a first plane; and
a plurality of detector elements disposed adjacent to the light source with at least a first of the detector elements being arranged on the first portion and at least a second of the detector elements being arranged on the second portion, each of the detector elements having a photodetection surface and the photodetection surface of the first detector element being oriented in the first plane and the photodetection surface of the second detector element being oriented in a second plane that is different from the first plane, wherein each detector element of the plurality of detector elements is configured to sense a reflection of light that is emitted by the emitter surface and reflected onto the respective detector element.

2. The implantable medical device of claim 1, wherein the plurality of detector elements are arranged in a three-dimensional array of detector elements.

3. The implantable medical device of claim 1, wherein at least a first detector element is arranged in a first spatial position and a second detector element is arranged in a second spatial position that is different from the first spatial position in at least two dimensions.

4. The implantable medical device of claim 1, further comprising a housing that defines a surface comprising a parabolic cross-section, wherein at least some of the plurality of detector elements are coupled to the surface.

5. The implantable medical device of claim 1, wherein at least one of the detector elements comprises a photodiode.

6. The implantable medical device of claim 1, wherein the plurality of detector elements are symmetrically arranged around the light source.

7. The implantable medical device of claim 1, further comprising a housing, wherein the light source and the detector elements are arranged on a common side of the housing.

8. The implantable medical device of claim 7, wherein the housing defines a recess and the light source and the detector elements are disposed in the recess.

9. The implantable medical device of claim 7, wherein the housing defines the surface having the planar profile and the curvilinear profile.

10. The implantable medical device of claim 7, wherein the housing defines a first surface and a second surface, and the light source is coupled to the first surface and at least one of the detector elements of the detector array is coupled to the second surface.

11. The implantable medical device of claim 1, wherein the plurality of detector elements at least partially surround the light source.

12. The implantable medical device of claim 11, wherein the plurality of detector elements surround the light source.

13. The implantable medical device of claim 1, wherein at least two detector elements of the plurality of detector elements have different angular orientations relative to each other.

14. The implantable medical device of claim 1, wherein each detector element of the plurality of detector elements comprises a photodetection surface, wherein the photodetection surfaces of the at least two detector elements are nonparallel.

15. The system implantable medical device of claim 1, wherein the light source comprises at least one of a red light emitting diode or an infrared light emitting diode.

16. The implantable medical device of claim 1, wherein the plurality of detector elements have a fixed position relative to the light source.

17. An implantable medical device comprising:
an outer housing surface including a first portion configured having a planar profile and a second portion of the surface configured having a curvilinear profile;
a light source disposed on the first portion having an emitter surface oriented in a first plane; and
at least two detectors that are arranged on the surface with a first of the at least two detectors being positioned on the first portion and a second of the at least two detectors being positioned on the second portion adjacent to the first portion, wherein at least a first of the detectors has a photodetection surface that is oriented in the first plane and a second of the detectors is oriented in a second plane that is different from the first plane and each of the at least two detectors is configured to generate a signal indicative of an intensity of a reflection of light emitted by the light source that is reflected onto each detector.

18. The implantable medical device of claim 17, wherein the detectors comprise an annular shape.

19. The implantable medical device of claim 17, wherein the at least two detectors are arranged in a concentric pattern.

20. The implantable medical device of claim 17, wherein the at least two detectors are nonplanar.

21. The implantable medical device of claim 17, wherein the at least two detector elements are arranged in a nonplanar configuration.

22. The implantable medical device of claim 21, wherein the at least two detector elements are arranged in three-dimensional array.

23. The implantable medical device of claim 21, wherein the at least two detector elements are located equidistant from the light source.

24. The implantable medical device of claim 17, wherein a first of the at least two detectors is located on a first side of the light source and a second of the at least two detectors is located on a second side of the light source, wherein the first side is opposite the second side.

25. A method comprising:
transmitting light from a light source positioned on a first outer surface of an implantable medical device housing having a first planar profile; and
receiving the light at a detector positioned on the housing, wherein the detector comprises a plurality of detector elements and at least a first of the detector elements is positioned on the first outer surface on a common plane with the light source and a second of the detector elements is positioned on a second surface having a second profile that is different from the first profile, wherein the second profile includes a plane that is at an angle relative to the plane of the first outer surface.

26. The implantable medical device of claim 1, wherein the at least one of the photodetection surfaces being oriented at a first angle relative to an axis that is perpendicular to the first plane and a second of the photodetection surfaces being oriented at a second angle that is different from the first angle.

* * * * *